US012697171B2

(12) United States Patent
Nguyen

(10) Patent No.: US 12,697,171 B2
(45) Date of Patent: *Aug. 4, 2026

(54) LESION CROSSING SHOCK WAVE CATHETER

(71) Applicant: Shockwave Medical, Inc., Santa Clara, CA (US)

(72) Inventor: Hoa Nguyen, San Jose, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 18/673,697

(22) Filed: May 24, 2024

(65) Prior Publication Data

US 2024/0307119 A1 Sep. 19, 2024

Related U.S. Application Data

(63) Continuation of application No. 17/901,351, filed on Sep. 1, 2022, now Pat. No. 12,023,098.

(Continued)

(51) Int. Cl.
*A61B 18/26* (2006.01)
*A61B 17/22* (2006.01)

(52) U.S. Cl.
CPC .... *A61B 18/26* (2013.01); *A61B 2017/22025* (2013.01); *A61B 2018/263* (2013.01)

(58) Field of Classification Search
CPC .......... A61B 18/26; A61B 2017/22025; A61B 2018/263; A61B 2017/22024;

(Continued)

(56) References Cited

U.S. PATENT DOCUMENTS

| | | |
|---|---|---|
| 2,916,647 A | 12/1959 | George |
| 3,412,288 A | 11/1968 | Ostrander |

(Continued)

FOREIGN PATENT DOCUMENTS

| | | |
|---|---|---|
| AU | 2009313507 B2 | 11/2014 |
| AU | 2013284490 B2 | 5/2018 |

(Continued)

OTHER PUBLICATIONS

Extended European Search Report and Written Opinion received for European Patent Application No. 22879375.8 mailed on Jul. 17, 2025, 8 pages.

(Continued)

*Primary Examiner* — Jonathan T Kuo
(74) *Attorney, Agent, or Firm* — Morrison & Foerster LLP

(57) ABSTRACT

The present invention provides a catheter for treating occlusions in body lumens. The catheter includes a catheter body that is fillable with fluid. An impactor is connected to the distal end of the catheter body and has a proximal end inside the catheter body and a distal end outside the catheter body. The catheter also includes a shock wave source configured to generate a shock wave, and a deflector coupled to the proximal end of the impactor in between the shock wave source and distal end of the catheter body. When the shock wave source generates a shock wave, the shock wave impinges on the deflector causing the deflector to advance in a forward direction in conjunction with the impactor such that the distal end of the impactor delivers a mechanical force to the occlusion to restore flow to the body lumen.

32 Claims, 10 Drawing Sheets

Related U.S. Application Data

(60) Provisional application No. 63/349,995, filed on Jun. 7, 2022, provisional application No. 63/252,467, filed on Oct. 5, 2021.

(58) Field of Classification Search
CPC .... A61B 2017/22094; A61B 17/22012; A61B 17/2202; A61B 17/22022
See application file for complete search history.

(56) References Cited

U.S. PATENT DOCUMENTS

| | | | |
|---|---|---|---|
| 3,413,976 A | 12/1968 | Roze | |
| 3,524,101 A | 8/1970 | Barbini | |
| 3,583,766 A | 6/1971 | Padberg | |
| 3,785,382 A | 1/1974 | Schmidt-Kloiber et al. | |
| 3,902,499 A | 9/1975 | Shene | |
| 3,942,531 A | 3/1976 | Hoff et al. | |
| 4,027,674 A | 6/1977 | Tessler et al. | |
| 4,030,505 A | 6/1977 | Tessler | |
| 4,445,509 A | 5/1984 | Auth | |
| 4,662,126 A | 5/1987 | Malcolm | |
| 4,662,375 A | 5/1987 | Hepp et al. | |
| 4,671,254 A | 6/1987 | Fair | |
| 4,685,458 A | 8/1987 | Leckrone | |
| 4,741,405 A | 5/1988 | Moeny et al. | |
| 4,809,682 A | 3/1989 | Forssmann et al. | |
| 4,813,934 A | 3/1989 | Engelson et al. | |
| 4,878,495 A | 11/1989 | Grayzei | |
| 4,890,603 A | 1/1990 | Filler | |
| 4,900,303 A | 2/1990 | Lemelson | |
| 4,990,134 A | 2/1991 | Auth | |
| 4,994,032 A | 2/1991 | Sugiyama et al. | |
| 5,009,232 A | 4/1991 | Hassler et al. | |
| 5,046,503 A | 9/1991 | Schneiderman | |
| 5,057,103 A | 10/1991 | Davis | |
| 5,057,106 A | 10/1991 | Kasevich et al. | |
| 5,061,240 A | 10/1991 | Cherian | |
| 5,078,717 A | 1/1992 | Parins et al. | |
| 5,102,402 A | 4/1992 | Dror et al. | |
| 5,103,804 A | 4/1992 | Abele et al. | |
| 5,116,227 A | 5/1992 | Levy | |
| 5,152,767 A | 10/1992 | Sypal et al. | |
| 5,152,768 A | 10/1992 | Bhatta | |
| 5,154,722 A | 10/1992 | Filip et al. | |
| 5,176,675 A | 1/1993 | Watson et al. | |
| 5,195,508 A | 3/1993 | Muller et al. | |
| 5,245,988 A | 9/1993 | Einars et al. | |
| 5,246,447 A | 9/1993 | Rosen et al. | |
| 5,254,121 A | 10/1993 | Manevitz et al. | |
| 5,281,231 A | 1/1994 | Rosen et al. | |
| 5,295,958 A | 3/1994 | Shturman | |
| 5,304,134 A | 4/1994 | Kraus et al. | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,454,809 A | 10/1995 | Janssen | |
| 5,472,406 A | 12/1995 | de la Torre et al. | |
| 5,582,578 A | 12/1996 | Zhong et al. | |
| 5,584,843 A | 12/1996 | Wulfman et al. | |
| 5,603,731 A | 2/1997 | Whitney | |
| 5,609,606 A | 3/1997 | O'Boyle | |
| 5,662,590 A | 9/1997 | de la Torre et al. | |
| 5,709,676 A | 1/1998 | Alt | |
| 5,846,218 A | 12/1998 | Brisken et al. | |
| 5,891,089 A | 4/1999 | Katz et al. | |
| 5,893,840 A | 4/1999 | Hull et al. | |
| 5,931,805 A | 8/1999 | Brisken | |
| 6,007,530 A | 12/1999 | Dornhofer et al. | |
| 6,033,371 A | 3/2000 | Torre et al. | |
| 6,056,722 A | 5/2000 | Jayaraman | |
| 6,080,119 A | 6/2000 | Schwarze et al. | |
| 6,083,232 A | 7/2000 | Cox | |
| 6,090,104 A | 7/2000 | Webster et al. | |
| 6,113,560 A | 9/2000 | Simnacher | |
| 6,132,444 A | 10/2000 | Shturman et al. | |
| 6,146,358 A | 11/2000 | Rowe | |
| 6,186,963 B1 | 2/2001 | Schwarze et al. | |
| 6,210,408 B1 | 4/2001 | Chandrasekaran et al. | |
| 6,215,734 B1 | 4/2001 | Moeny et al. | |
| 6,217,531 B1 | 4/2001 | Reitmajer | |
| 6,267,747 B1 | 7/2001 | Samson et al. | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,364,894 B1 | 4/2002 | Healy et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,440,124 B1 | 8/2002 | Esch et al. | |
| 6,494,890 B1 | 12/2002 | Shturman et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,666,834 B2 | 12/2003 | Restle et al. | |
| 6,689,089 B1 | 2/2004 | Tiedtke et al. | |
| 6,736,784 B1 | 5/2004 | Menne et al. | |
| 6,740,081 B2 | 5/2004 | Hilal | |
| 6,755,821 B1 | 6/2004 | Fry | |
| 6,939,320 B2 | 9/2005 | Lennox | |
| 6,989,009 B2 | 1/2006 | Lafontaine | |
| 7,066,904 B2 | 6/2006 | Rosenthal et al. | |
| 7,087,061 B2 | 8/2006 | Chernenko et al. | |
| 7,241,295 B2 | 7/2007 | Maguire | |
| 7,309,324 B2 | 12/2007 | Hayes et al. | |
| 7,389,148 B1 | 6/2008 | Morgan | |
| 7,505,812 B1 | 3/2009 | Eggers et al. | |
| 7,569,032 B2 | 8/2009 | Naimark et al. | |
| 7,850,685 B2 | 12/2010 | Kunis et al. | |
| 7,853,332 B2 | 12/2010 | Olsen et al. | |
| 7,873,404 B1 | 1/2011 | Patton | |
| 7,951,111 B2 | 5/2011 | Drasler et al. | |
| 8,162,859 B2 | 4/2012 | Schultheiss et al. | |
| 8,177,801 B2 | 5/2012 | Kallok et al. | |
| 8,353,923 B2 | 1/2013 | Shturman | |
| 8,556,813 B2 | 10/2013 | Cioanta et al. | |
| 8,574,247 B2 | 11/2013 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Hakala et al. | |
| 9,138,249 B2 | 9/2015 | Adams et al. | |
| 9,198,825 B2 | 12/2015 | Katragadda et al. | |
| 9,333,000 B2 | 5/2016 | Hakala et al. | |
| 9,421,025 B2 | 8/2016 | Hawkins et al. | |
| 9,433,428 B2 | 9/2016 | Hakala et al. | |
| 9,522,012 B2 | 12/2016 | Adams | |
| 9,642,673 B2 | 5/2017 | Adams et al. | |
| 9,717,513 B2 | 8/2017 | Golan | |
| 9,993,292 B2 | 6/2018 | Adams | |
| 10,039,561 B2 | 8/2018 | Adams et al. | |
| 10,118,015 B2 | 11/2018 | De La Rama et al. | |
| 10,149,690 B2 | 12/2018 | Hawkins et al. | |
| 10,154,799 B2 | 12/2018 | Van Der Weide et al. | |
| 10,159,505 B2 | 12/2018 | Hakala et al. | |
| 10,206,698 B2 | 2/2019 | Hakala et al. | |
| 10,226,265 B2 | 3/2019 | Ku et al. | |

(56) References Cited

U.S. PATENT DOCUMENTS

| | | |
|---|---|---|
| 10,420,569 B2 | 9/2019 | Adams |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,464,528 B2 | 10/2022 | Brady et al. |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 12,023,098 B2 | 7/2024 | Nguyen |
| 12,239,371 B2 | 3/2025 | Tschida et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0142754 A1 | 6/2006 | Irion et al. |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0214061 A1 | 7/2014 | Adams et al. |
| 2015/0157399 A1 | 6/2015 | Romoscanu |
| 2015/0320432 A1 | 11/2015 | Adams |
| 2016/0151081 A1 | 6/2016 | Adams et al. |
| 2016/0184022 A1 | 6/2016 | Grace |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2018/0098779 A1 | 4/2018 | Betelia et al. |
| 2019/0150960 A1 | 5/2019 | Nguyen et al. |
| 2019/0388110 A1 | 12/2019 | Nguyen |
| 2021/0085347 A1 | 3/2021 | Phan et al. |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0107690 A1 | 4/2023 | Nguyen |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 113038898 A | 6/2021 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A | 11/2010 |
| EP | 2362798 B1 | 4/2014 |
| JP | S61-217147 A | 9/1986 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |

(56)        References Cited

FOREIGN PATENT DOCUMENTS

| | | | |
|---|---|---|---|
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2010214053 | A | 9/2010 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| JP | 2019521802 | A | 8/2019 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009027846 | A2 | 3/2009 |
| WO | WO-2009121017 | A1 | 10/2009 |
| WO | WO-2009126544 | A1 | 10/2009 |
| WO | WO-2009136268 | A2 | 11/2009 |
| WO | WO-2009152352 | A2 | 12/2009 |
| WO | WO-2010014515 | A2 | 2/2010 |
| WO | WO-2010054048 | A2 | 5/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2016109731 | A1 | 7/2016 |
| WO | WO-2018022641 | A1 | 2/2018 |
| WO | WO-2018083666 | A1 | 5/2018 |
| WO | WO-2019099218 | A1 | 5/2019 |
| WO | WO-2020256949 | A1 | 12/2020 |

OTHER PUBLICATIONS

Office Action received for Brazilian Patent Application No. 11 2024 005867 0, dated Mar. 7, 2025, 9 pages. English Translation.

Office Action received for German Patent Application No. 11 2022 004 783.6, mailed on Apr. 7, 2025, 6 pages. English Translation.

Office Action received for Japanese Patent Application No. 2024-520009, mailed on Dec. 5, 2025, 15 pages. English Translation.

Notice of Allowance received for Brazilian Patent Application No. 11 2024 005867 0, mailed on Jun. 24, 2025, 5 pages.

Notice of Allowance received for Chinese Patent Application No. 202280067045.3, mailed on May 21, 2025, 4 pages. English translation.

Notice of Allowance received for German Patent Application No. 11 2022 004 783.6, mailed on Sep. 9, 2025, 5 pages. English Translation.

Notice of Allowance received for Singaporean Application No. 11202401653W, mailed on Feb. 4, 2025, 2 pages.

BD, (2023). "Crosser™ CTO recanalization catheters," available online at <https://web.archive.org/web/20230923002642/https:/www.bd.com/en-us/products-and-solutions/products/product-families/crosser-cto-recanalization-catheters#overview>, 2 pages.

Boston Scientific, (2015). "Swiss LithoClast™ Select, Lithotripter," available online at <https://www.bostonscientific.com/en-US/products/lithotripsy/swiss-lithoclast.html>, 4 pages.

International Search Report and Written Opinion received for International Patent Application No. PCT/US2022/075903 mailed on Dec. 21, 2022, 8 pages.

Medinol, (2017). "Piculet™, CTO Crossing Device," available online at <https://web.archive.org/web/20170517130850/http:/medinol.com/us/products/piculet>, 4 pages.

SoundBite Medical, (2021). "SoundBite Medical: Our Technology," available online at <https://web.archive.org/web/20210731160502/http:/soundbitemedical.com/our-technology/>, 4 pages.

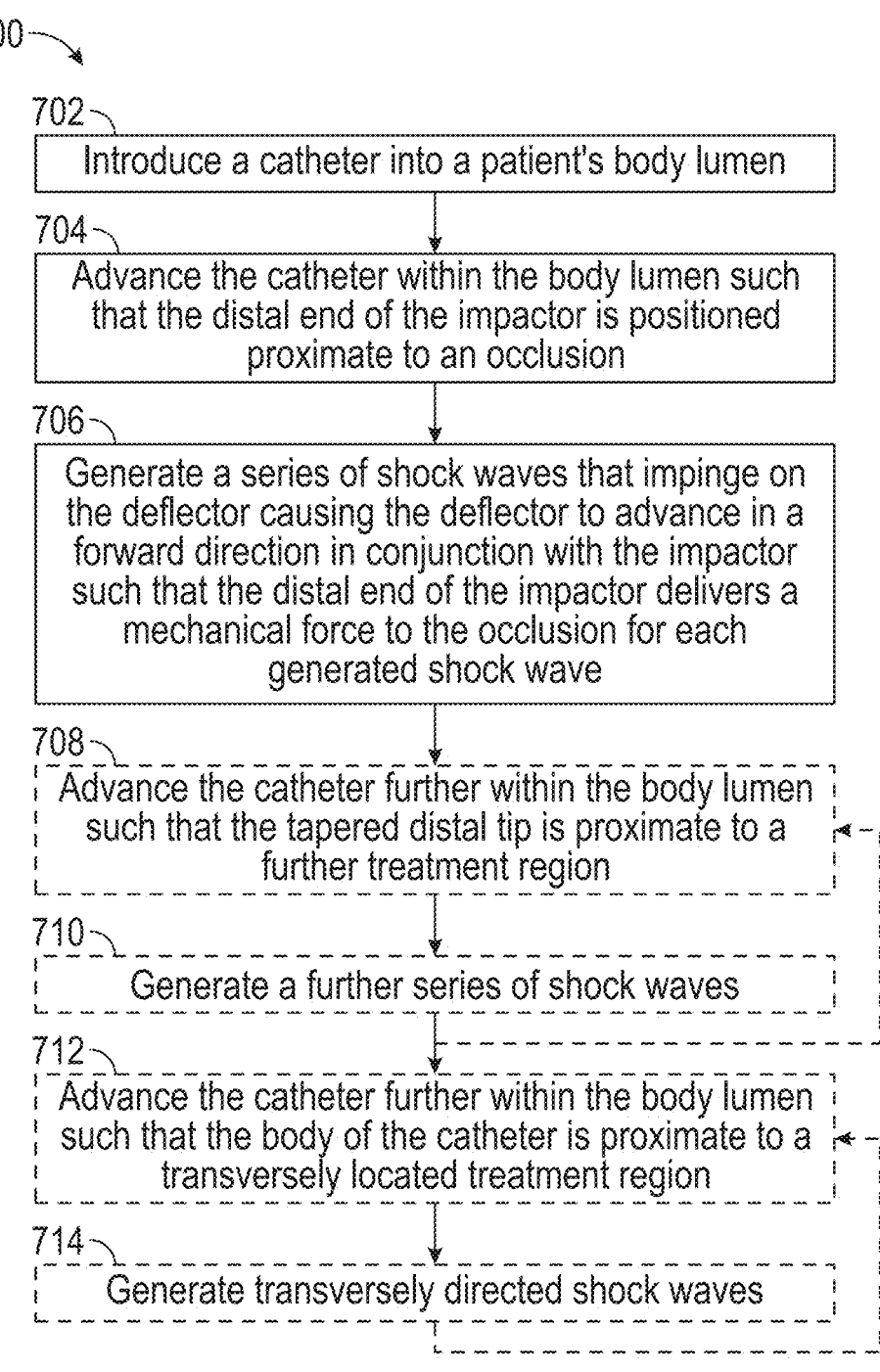

700

702 — Introduce a catheter into a patient's body lumen

704 — Advance the catheter within the body lumen such that the distal end of the impactor is positioned proximate to an occlusion 706 — Generate a series of shock waves that impinge on the deflector causing the deflector to advance in a forward direction in conjunction with the impactor such that the distal end of the impactor delivers a mechanical force to the occlusion for each generated shock wave 708 — Advance the catheter further within the body lumen such that the tapered distal tip is proximate to a further treatment region 710 — Generate a further series of shock waves 712 — Advance the catheter further within the body lumen such that the body of the catheter is proximate to a transversely located treatment region 714 — Generate transversely directed shock waves

FIG. 7

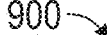
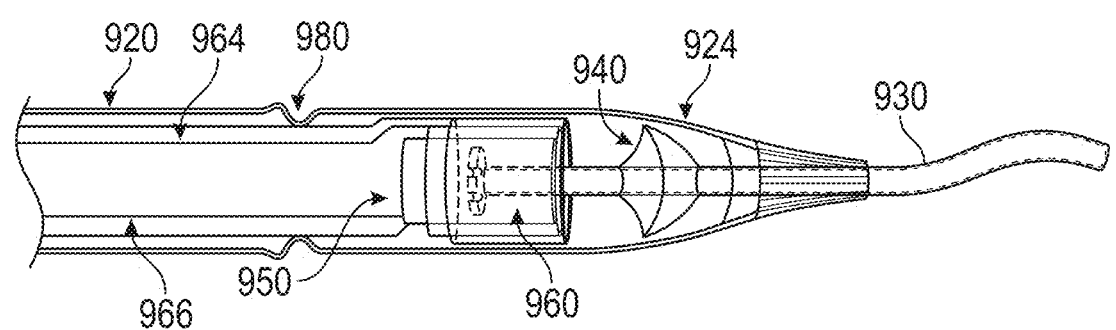
FIG. 9A
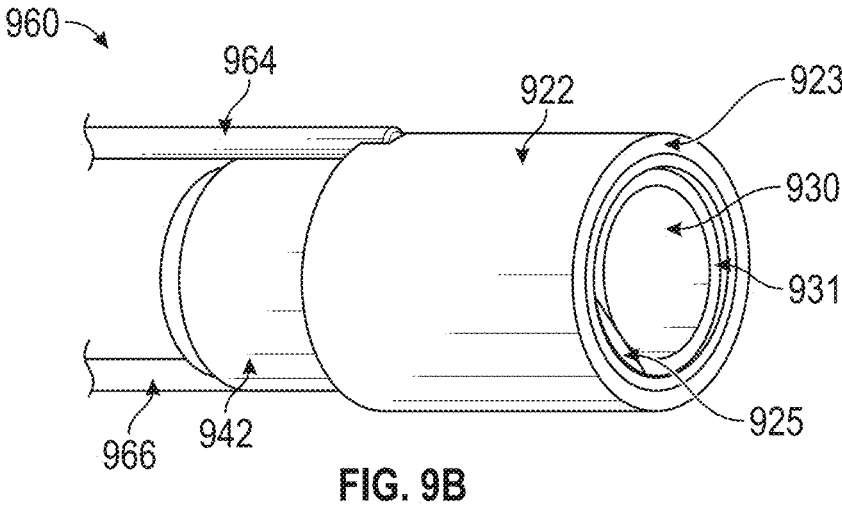
FIG. 9B

LESION CROSSING SHOCK WAVE CATHETER

CROSS REFERENCE TO RELATED APPLICATIONS

This application is a continuation of U.S. patent application Ser. No. 17/901,351, filed on Sep. 1, 2022, which claims the benefit of U.S. Provisional Application No. 63/252,467, filed on Oct. 5, 2021, and U.S. Provisional Application No. 63/349,995, filed on Jun. 7, 2022, the entire contents of each of which are incorporated herein by reference.

FIELD OF THE DISCLOSURE

The present disclosure relates generally to the field of medical devices and methods, and more specifically to catheter devices for treating occlusions in body lumens, such as vascular or urinary lumens.

BACKGROUND

The subject invention relates generally to a catheter for treating occlusions in a body lumen, such as kidney stones, calcified lesions in vasculature, a partial coronary occlusion, or a chronic total coronary occlusion to restore flow to the lumen.

Chronic total occlusions ("CTOs") in vasculature remain the "final frontier" of percutaneous intervention. When arteries are partially or totally occluded with thrombus, plaque, fibrous plaque, or calcium deposits, intervention to remove the occlusions becomes much riskier to patients, and much more complicated and time-consuming for physicians. Left untreated, CTOs reduce blood flow to the heart and peripheral limbs and can cause critical ischemia and amputations.

In a typical CTO intervention, a physician first passes a soft narrow guide wire through a blood vessel to puncture the occluded area and reach the distal true lumen of the vessel. An angioplasty balloon can then feed down the blood vessel on the guide wire to the location of the blockage and pressurized to reduce or break the calcified plaques.

While a wide variety of catheters have been developed to treat arterial disease, few commercial devices yield high success rates for CTO treatment. Existing treatment systems for percutaneous coronary angioplasty or peripheral angioplasty, like balloon catheters, are ill suited for crossing the resistant fibrotic and calcified tissues common in CTOs. Conventional guide wires may have difficulty penetrating the thick, fibrous caps of CTOs, and risk trauma to blood vessel walls when navigating narrow and tortuous regions of vasculature. Attempting to penetrate a CTO using a soft guide wire can cause buckling (e.g., deflection of the guide wire to a subintimal passage or collateral branch), and stiffer guide wires must be used very carefully to avoid penetrating the arterial wall when forced against a total occlusion. Even if the initial puncture with a guide wire is successful, placement of dilation devices, like angioplasty balloons, can be very difficult in chronically occluded vessels. This makes the treatment of CTOs a technically challenging procedure that requires a long learning curve for interventional cardiologists.

Recently, catheters have been developed that include one or more shock wave sources (e.g., electrode pairs) for generating shock waves inside an angioplasty balloon. Shock wave devices can be particularly effective for treating calcified lesions because the acoustic waves can crack lesions near the angioplasty balloon without harming the surrounding vasculature. In these devices, a catheter can be advanced over a guide wire in a patient's vasculature until it is proximal to a lesion. A balloon is then inflated with conductive fluid to contact the lesion and high voltage pulses are applied across the electrode pairs to produce shock waves that direct acoustic waves into the lesion. Once the lesions are cracked, the balloon can be expanded further in the vessel to create an improved blood flow in the lumen. Efforts have been made to direct acoustic energy from the shock waves in a forward direction to break up tighter and harder-to-cross occlusions in vasculature. Examples of forward-firing designs can be found in U.S. Pat. No. 10,966, 737 and U.S. Publication Nos. 2019/0388110, both of which are incorporated herein by reference.

While shock wave catheter designs have been deployed in both coronary and peripheral vessel applications, even those designs have difficulty crossing chronic partial or total occlusions in vasculature.

Some currently available devices for treating CTOs use ultrasound, piezoelectric crystals, or linear acoustic shock wave sources to deliver mechanical energy to break up chronic occlusions. Often, these devices direct intense mechanical vibrations along a guide wire to drill out fibrotic and calcified tissues in vasculature. However, these systems require bulky and expensive generators to operate, and the intensity of the vibrations may make the guide wires difficult to control, risking damage to blood vessel walls during treatment. Other systems use a mechanical hammer that can be introduced over a guide wire to deliver mechanical energy to resistant CTOs. However, these systems face similar issues. Even further systems direct radio frequency energy along a guide wire to disrupt occlusions. However, radio frequency energy generates heat and plasma within blood vessels, and the guide wires in such systems must be carefully centered and continuously moved to avoid burning blood vessel walls.

In addition to these problems, many existing systems for treating CTOs require multiple devices to complete an intervention, for instance, one device for penetrating an occlusion and another device for modifying calcified tissue proximate to vessel walls. Accordingly, there is an unmet need for a device that can penetrate resistant fibrotic and calcified tissue to treat CTOs without expensive generators, multiple devices, and unnecessary risk of trauma to blood vessels.

Similar devices are needed for occlusions formed in other parts of the body, for examples, kidney stones in a ureter.

BRIEF SUMMARY

The above objects are realized in a catheter that includes an impactor for delivering mechanical force directly to an occlusion in a body lumen, such as a stenotic lesion in a patient's vasculature or a kidney stone in a ureter. In some designs, the impactor is a flexible guide wire coupled to the distal end of the catheter body and having a distal tip outside of the catheter body. In other examples, the impactor is a flexible hollow member having a lumen for receiving a guide wire. The proximal end of the impactor is coupled to a deflector that is configured to slide forward and backward within the catheter body. When a shock wave is generated within the catheter body, the shock wave impinges on the deflector causing the deflector to advance in a forward direction. The distal end of the impactor is driven into the occlusion in conjunction with the deflector to deliver mechanical force to the occlusion. Repeated shock waves cause the deflector and the impactor to oscillate and produce a "jackhammer effect" that ruptures the occlusion and restores flow to the lumen.

An exemplary invention provides a catheter for treating an occlusion in a body lumen. The catheter includes a catheter body having a distal end, the catheter body being fillable with a fluid. The catheter also includes an impactor connected to the distal end of the catheter body, the impactor having a proximal end inside the catheter body and a distal end outside the catheter body. The catheter also includes a shock wave source configured to generate a shock wave, and a deflector coupled to the proximal end of the impactor in between the shock wave source and distal end of the catheter body. When the shock wave source generates a shock wave, the shock wave impinges on the deflector causing the deflector to advance in a forward direction in conjunction with the impactor such that the distal end of the impactor delivers a mechanical force to the occlusion.

An exemplary method for treating an occlusion in a body lumen includes introducing a catheter into a patient's body lumen. The catheter includes a catheter body having a distal end, the catheter body being fillable with a conductive fluid. The catheter also includes an impactor connected to the distal end of the catheter body, the impactor having a proximal end inside the catheter body and a distal end outside the catheter body. The catheter further includes a shock wave source configured to generate a shock wave in the catheter body, and a deflector coupled to the proximal end of the impactor in between the shock wave source and distal end of the catheter body. The method also includes advancing the catheter within the body lumen such that the distal end of the impactor is positioned proximate to the occlusion. The method also includes applying a high voltage pulse across the shock wave source to generate a shock wave. When the shock wave source generates a shock wave, the shock wave impinges on the deflector causing the deflector to advance in a forward direction in conjunction with the impactor such that the distal end of the impactor delivers a mechanical force to the occlusion.

DESCRIPTION OF THE FIGURES

Illustrative aspects of the present disclosure are described in detail below with reference to the following drawing figures. It is intended that that embodiments and figures disclosed herein are to be considered illustrative rather than restrictive.

FIG. 7 is a flow chart of a method of using a catheter to treat an occlusion in a body lumen, according to aspects of the present disclosure.

FIG. 9A is an illustration of a distal end of a catheter having a tapered distal tip and a coaxial emitter, according to aspects of the present disclosure.

FIG. 9B shows an exemplary coaxial emitter shock wave source, according to aspects of the present disclosure.

DETAILED DESCRIPTION

Figure 1:
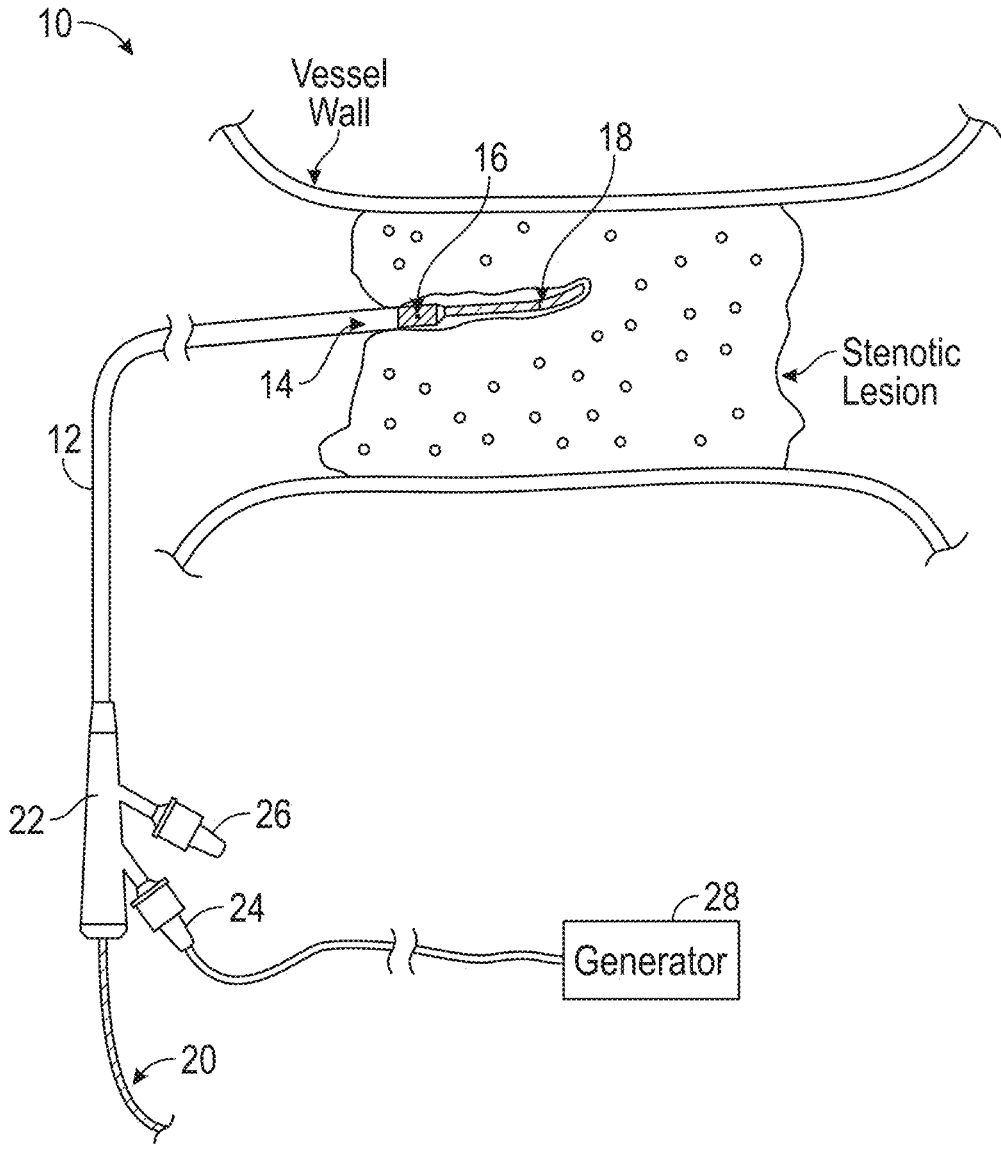
FIG. 1 is an illustration of a catheter being used to treat a stenotic lesion in a blood vessel, according to aspects of the present disclosure.

The following description is presented to enable a person of ordinary skill in the art to make and use the various embodiments disclosed herein. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments and aspects thereof are not intended to be limited to the examples described herein and shown but are to be accorded the scope consistent with the claims.

The present disclosure relates generally to a catheter system for treating occlusions in a body lumen, such as a CTO or circumferential calcium in a patient's vasculature or a kidney stone in a patient's ureter. The catheters described herein incorporate impactor elements that deliver mechanical forces directly into occlusions in a body lumen to permit treatment of tighter and harder-to-cross calcific lesions and CTOs. The present invention is similar to existing intravascular lithotripsy systems in that it can comprise one or more shock wave sources (e.g., electrode pairs) on a catheter that is entered into a body lumen of a patient to treat an occlusion. However, the catheter of the present invention additionally includes an impactor (e.g., an impacting member, such as a guide wire or a flexible hollow member) connected to a distal end of the catheter body. The impactor has a proximal end that is coupled to a deflector inside the catheter body, and a distal end outside of the catheter body that is adapted for mechanically impacting occlusions. When a shock wave is generated at a shock wave source inside the catheter body, at least a portion of the shock wave energy impinges on the deflector causing it to advance forward in conjunction with the impactor. When the deflector advances forward within the catheter body, the distal tip of the impactor advances forward in the body lumen to deliver a mechanical force directly to an occlusion. The distal end of the catheter body has flexible material properties that allow the impactor to advance forward responsive to a shock wave. When the shock wave terminates, the material properties of the distal end cause the impactor and the deflector to return backward to their original positions within the catheter body. In some examples, the deflector is coupled to a centering mechanism that maintains the deflector and impactor at approximately a central axis of the catheter body while permitting forward and backward movement along the central axis.

Generating repeated shock waves cause the deflector to oscillate inside the catheter body. The deflector transfers mechanical energy to the impactor to cause vibrations at the distal tip of the impactor produce an oscillating "jackhammer effect" for clearing occlusions from a body lumen. Advantageously, incorporating impactor elements that deliver direct mechanical forces to occlusions enables the catheter to puncture and cross resistant and fibrous regions in a body lumen, such as calcified and fibrotic tissues and CTOs, that are difficult to treat through traditional angioplasty methods. This allows the catheter to advance into and treat even tighter regions of a body lumen, such as those that are partially or totally occluded, to restore normal flow to the lumen.

In addition to impinging on the deflector to produce oscillations at the impactor, at least a portion of the shock wave energy may be transmitted (e.g., propagated and/or deflected by the deflector) in a direction transverse to the catheter. This transverse shock wave energy propagates through walls of the catheter body to treat regions of a body lumen proximal to the catheter body, such as calcified regions that have formed on walls of the lumen. Paired with the impactor's forward-directed jackhammering, this transverse shock wave energy allows the catheter to continuously treat larger areas of an occluded vessel (e.g., both total occlusions distal to the catheter and calcified tissues surrounding the catheter) and may reduce the need for multiple devices during treatment of an occluded body lumen. Once a total occlusion has been disrupted (e.g., penetrated by the impactor to provide a space for entry of the distal end of the catheter body), the catheter may be advanced further into the body lumen and shock wave treatment can be continued to reduce calcified tissues surrounding the catheter.

FIG. 1 illustrates an exemplary catheter 10 for treating an occlusion in a body lumen. The catheter 10 can be introduced into an occlusion in a patient's vasculature, such as the stenotic lesion depicted in FIG. 1, using a removable guide wire 20 or an elongated impactor 18 connected to the distal end 14 of the catheter body 12. During treatment, the catheter body 12 is advanced in the lumen until the distal tip of the impactor 18 abuts against an occlusion and/or the distal end 14 of the catheter body 12 is positioned proximate to a calcified region of the lumen. In some examples, the catheter body 12 has compliant material properties such that the catheter can be torqued, curved, and physically manipulated to maneuver the catheter 10 to the site of the occlusion within the body lumen.

The distal end 14 of the catheter body 12 is connected to an elongated impactor 18, such as a portion of a guide wire or a hollow elongated member with a lumen sized to receive a guide wire (e.g., removable guide wire 20). The distal end 14 surrounds a shock wave source 16, such that the shock waves are produced in a closed system defined by the walls of the catheter body 12. The shock wave source 16 generates shock waves at a plurality of emitters (e.g., electrode pairs) to produce acoustic waves that propagate through the distal end 14 of the catheter body 12. In some examples, an electrode pair may be formed from one or more insulated wires having exposed portions (e.g., an exposed distal tip or an insulation-removed portion of the wire) and one or more conductive emitter bands (e.g., conductive metal sheaths) mounted within the catheter body 12 and surrounding the exposed portions of the wires. The electrode pairs may be arranged in a low-profile configuration that reduces the diameter of the distal end 14 of the catheter 10 and permits the treatment of tighter, harder-to-cross lesions like the CTO (i.e., the stenotic lesion) depicted in FIG. 1. In some examples, an electrode pair can be formed from an outer conductive sheath mounted circumferentially around and concentric with an inner conductive sheath each connected to an insulated wire that are mounted within the catheter body 12. Alternatively, the electrode pair may be formed from a flat coil disposed within a conductive sheath, wherein both the flat coil and the conductive sheath are each connected to an insulated wire and mounted within the catheter body 12.

An exemplary catheter 10 also includes a proximal end 22 or handle that remains outside of the body lumen of the patient during treatment. The proximal end 22 includes a fluid port 26 for filling and evacuating (e.g., inflating and deflating) the catheter body 14 with conductive fluid. An electrical connection port 24 is also located on the proximal end 22 of the catheter 10 and provides an electrical connection between the shock wave source 16 and an external pulsed high voltage source 28, such as the generator shown in FIG. 1. In some examples, the proximal end 22 includes an entry port for receiving a removable guide wire 20 (e.g., a further guide wire to aid in insertion and advancement of the catheter into a body lumen in addition to the impactor 18 that impacts occlusions).

The catheter 10 also includes a catheter body 12 (e.g., a flexible hollow shaft) that extends between the proximal end 22 (i.e., the handle) and the distal end 14 (i.e., the end of the catheter body 12 housing the shock wave source 16 and coupled to the impactor 18). In some cases, one or more insulated wires extend along the length of the catheter body 12 to provide a connection between the high voltage source 28 and the one or more electrode pairs of the shock wave source(s) 16. In some examples, at least a portion of the catheter body 12 includes internal conduits connecting elements of the distal end 14 with the proximal end handle 22 of the catheter. For instance, one or more wire lumens may be provided for carrying the insulated wires that electrically connect the pulsed high voltage source 28 with electrodes of the distal shock wave source 16, and/or one or more fluid lumens (e.g., a fluid inlet lumen and a fluid outlet lumen) may be provided for carrying conductive fluid from the fluid port 26 to the distal end 14 of the catheter body 12. In some examples, e.g., examples where the catheter 10 is inserted using a removable guide wire, the catheter body 12 and/or the impactor 18 may include a guide wire lumen sized to receive a guide wire.

Figures 2, 3:
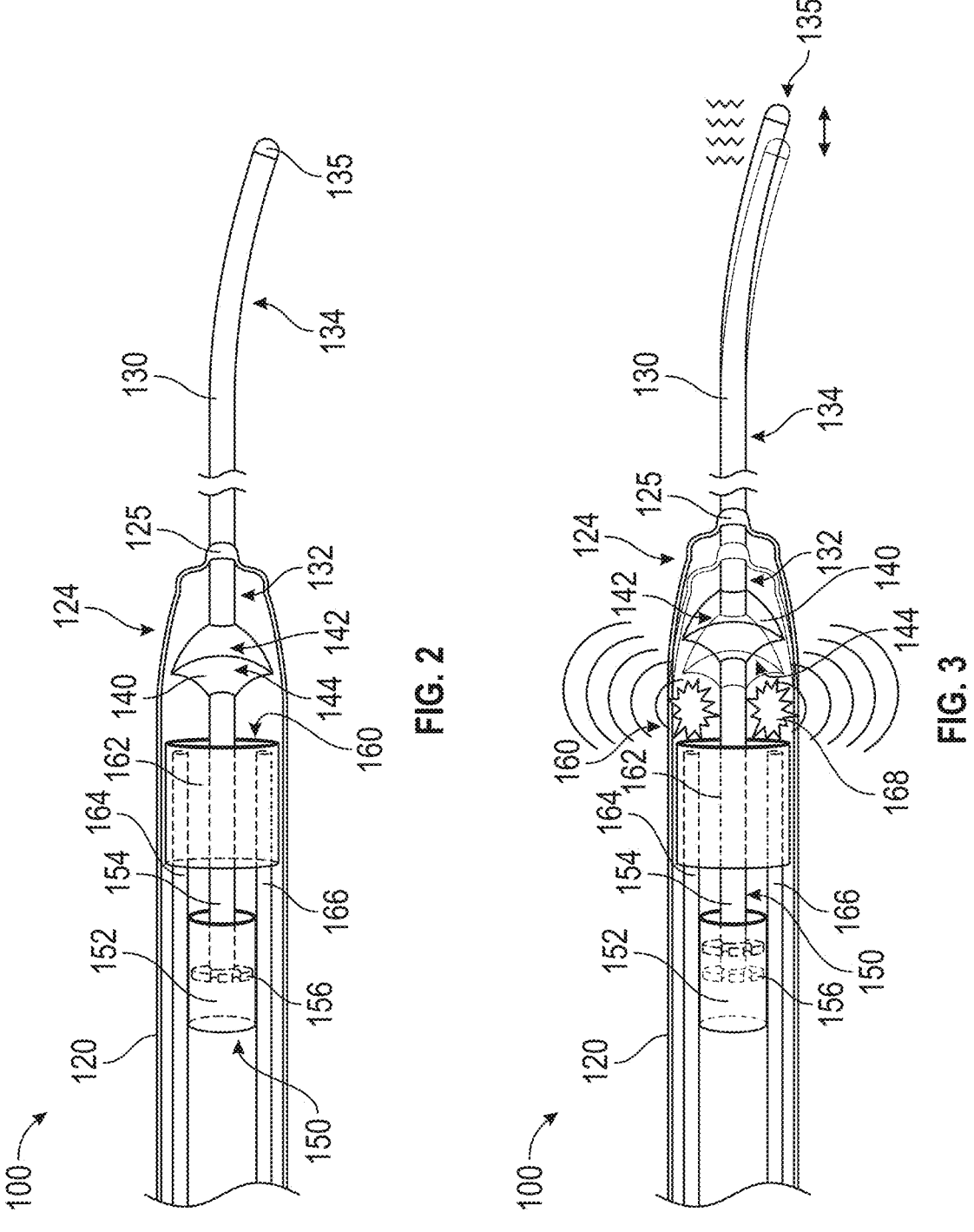
FIG. 2 is an illustration of a distal end of a catheter for treating an occlusion in a body lumen, according to aspects of the present disclosure.
FIG. 3 is an illustration of the distal end of the catheter of FIG. 2 generating shock waves that impinge on a deflector, according to aspects of the present disclosure.

FIGS. 2-3 illustrate an exemplary catheter for treating an occlusion in a body lumen, such as the catheter described in relation to FIG. 1. FIG. 2 provides a sectional view of a distal portion of the catheter. FIG. 3 provides a sectional view of the distal portion of the catheter while the catheter is generating shock waves to treat an occlusion in a body lumen.

Referring to FIG. 2, the catheter 100 includes a catheter body 120, a flexible impactor 130, a deflector 140, a centering mechanism 150, and a shock wave source 160. The impactor 130 is scaled to the distal end 124 of the catheter body 120 at a seal 125, and includes a proximal end 132 inside the catheter body 120 and a distal end 134 that remains outside the catheter body 120, the distal end 134 having a distal tip 135 for impacting occlusions in a body lumen. The deflector 140 is coupled to a proximal end 132 of the impactor 130 and is located between the shock wave source 160 and the distal end 124 of the catheter body 120, such that shock waves generated at the shock wave source 160 impinge on a back surface 144 of the deflector 140. The centering mechanism 150 is coupled to the proximal end of the deflector 140 and is adapted to maintain the deflector 140 and the impactor 130 along a central axis of the catheter 100 while permitting oscillating forward and backward movement of the deflector 140 within the catheter body 120. The centering mechanism includes a cylinder 152 mounted within the catheter body 120 and a shaft 154 configured to slide within the cylinder 152. One or more shock wave sources 160, e.g., one or more electrode pairs, generate shock waves within the catheter body 120 to advance the distal tip 135 of the impactor 130 into an occlusion. In some examples, as seen in FIGS. 2-3, the shock wave source 160 includes a conductive emitter band 162 mounted within the catheter and one or more insulated wires (e.g., a first insulated wire 164 and a second insulated wire 166) extending along the length of the catheter 100.

The catheter body 120 is a hollow elongated shaft having a proximal end (not shown), and a distal end 124. As used herein, the proximal end of the catheter body 120 refers to the end that is closest to the physician when the catheter 100 is in use, and the distal end 124 refers to the end of the catheter body 120 that is positioned proximate to a treatment site in a body lumen, e.g., an occlusion or region of calcified plaque in a blood vessel or a kidney stone in a ureter, and farthest from the physician controlling the catheter 100 from outside the lumen. In some examples, the proximal end of the catheter body 120 includes a handle of the catheter 100, e.g., the handle shown in FIG. 1.

The walls of the catheter body 120 define a cavity that surrounds the shock wave source 160 and is fillable with a conductive fluid, such as saline. The conductive fluid allows current to flow across electrodes of the shock wave source(s) 160 and allows shock waves to propagate from the shock wave source 160 to the deflector 140 and through the walls of the catheter body 120. In some embodiments, the conductive fluid may also contain an x-ray contrast to permit fluoroscopic viewing of the catheter 100 during use. Fluid may be flowed in and out of the catheter body 120 via a fluid inlet line and a fluid return line, respectively (not shown). The fluid inlet line may include a fluid inlet positioned at a proximal end of the catheter body 120 that flows fluid into the catheter body 120. The fluid return line may include a fluid inlet positioned near the distal end 124 of the catheter body 120 that draws in conductive fluid from the interior volume of the catheter body 120. In this way, the fluid inlet line and the fluid return line circulate the conductive fluid within the interior volume of the catheter body 120. Circulation of the conductive fluid may prevent bubbles and debris created by the shock wave source 160 from becoming trapped within the distal end 124 of the catheter body 120 due to the limited space within the tip. Furthermore, circulation of the conductive fluid may aid in cooling the catheter 100 and treatment site.

The distal end 124 of the catheter body 120 (e.g., at least the most distal 10 mm-20 mm portion of the catheter body) is formed from a flexible material, such as Pebax or polyurethane. The flexible material of the distal end 124 permits the impactor 130 to advance in a forward direction responsive to generation of a shock wave and causes the impactor 130 to return backward after the shock wave has terminated. The flexible material of the distal end 124 has compliant or semi-compliant material properties that allow the distal end 124 to extend or compress responsive to axial movement of the deflector 140 and impactor 130. In some examples, the distal end 124 of the catheter body 120 is shaped with features e.g., ridges or projecting features, that facilitate extension and compression of the distal end 124 in order to permit advancement of the impactor 130 and to effectuate backward movement of the impactor 130.

The catheter body 120 (e.g., a proximal end of the catheter body 120) may be formed from any desired material, for instance, a low-profile flexible or semi-compliant polymeric material such as Pebax or polyurethane. The distal end 124 may be integral to the catheter body 120 and formed from the same material or could be formed from a different material and attached to the rest of the catheter body 120 by way of, e.g., a laser bond or heat seal. In some examples, the catheter body 120 (e.g., a proximal end of the catheter body 120) is formed from a rigid material and the distal end 124 of the catheter body is formed from a relatively more flexible material.

In some examples, e.g., to facilitate treatment of regions of a body lumen proximate to and surrounding the catheter body 120, at least a portion of the catheter body is formed from a flexible material that is inflatable to increase a diameter of the catheter body 120. For instance, at least the distal end 124 of the catheter body 120 may be formed from an inflatable material. In such an example, the catheter body 120 can be inflated with conductive fluid such that, in an inflated state, the distal end 124 contacts surrounding walls of the body lumen and provides a space between the shock wave source 160 and the walls of the catheter body. The catheter body 120 may be inflated to a desired pressure, which may be between approximately one atmosphere and approximately six atmospheres. In some examples, the diameter of the catheter body 120 (e.g., the diameter of a flexible or semi-compliant distal end 124 of the catheter body 120) in an inflated state may be about 10-15% greater than the diameter of the catheter body 120 in a deflated state. However, in some examples the diameter of the catheter body 120 in an inflated state is less than 10% greater than the diameter of the catheter body 120 in a deflated state, or has an approximately equal diameter in both a deflated and an inflated state.

Prior to insertion or removal of the catheter 100 from the body lumen, the distal end 124 can be deflated to facilitate passage of the catheter body 120 through a body lumen. Additionally or alternatively, the catheter body 120 may be formed from a rigid material, such as a rigid or semi-compliant polymer that does not inflate when filled with conductive fluid.

The distal end 124 of the catheter body 120 surrounds the shock wave generator 160, such that the shock waves are produced in a closed system defined by the walls of the distal end 124. Accordingly, the flexible material of the distal end 124 allows for transmission of acoustic energy through the surface of the catheter body 120 and into regions of a body lumen located proximate to the surface of the catheter body 120. In some examples, the catheter body 120 and/or distal end 124 are formed from a heat-resistant material adapted to prevent accidental rupturing of the material caused by heat generated by the shock wave source 160 during shock wave treatment.

The distal end 124 of the catheter body 120 is connected to an impactor 130 and surrounds at least a portion of the proximal end 132 of the impactor 130. The distal end 124 of the catheter body 120 is connected to the impactor 130 at a seal 125, for instance, a laser bond, a heat seal, or an adhesive. In another example, the seal 125 is formed from a hole in the elastic material of the distal end 124 of the catheter body 120 having a smaller diameter than the elongated impactor 130, such that the hole compresses the perimeter of the impactor 130 to retain the impactor 130 in connection with the distal end 124. In other examples, the hole may be sized to loosely retain the impactor 130 in connection with the distal end 124. Other means of connecting the distal end 124 and the impactor 130 are also anticipated.

As used herein, the impactor 130 is an elongated flexible shafted member adapted for impacting an occlusion in a body lumen to deliver mechanical force directly to the occlusion. In some examples, the impactor 130 is a metal guide wire or a portion of a guide wire. In other examples, the impactor 130 is a hollow tube-like member having a lumen sized to receive a guide wire (e.g., the removable guide wire 20 of FIG. 1). The impactor 130 includes a proximal end 132 inside the catheter body 120 and a distal end 134 outside the catheter body 120 (e.g., external to the catheter body 120 but inside the body lumen) that includes a distal tip 135. The distal end 134 of the impactor 130 refers to the portion of the impactor 130 that is distal to the seal 125 between the impactor 130 and the distal end 124 of the catheter body 120, and the proximal end 132 of the impactor 130 refers to the portion that is proximal to the seal 125 between the deflector 130 and the distal end 124.

The proximal end 132 of the impactor 130 may terminate at the deflector 140. However, alternatively, the proximal end 132 may pass through the deflector 140 and terminate at the centering mechanism 150 (i.e., such that the shaft 154 of the centering mechanism 150 includes the proximal end 132 of the impactor 130). In yet further examples, the proximal end 132 of the impactor 130 extends through a shaft of the catheter body 120 and, in some cases, to a proximal end handle of the catheter 100 external to the body lumen (e.g., a handle controlled by a physician during advancement and use of the catheter, such as the handle 22 depicted in FIG. 1).

The distal end 134 of the impactor 130 remains outside the catheter body 120 and includes a distal tip 135 adapted to deliver mechanical force to an occlusion in a body lumen to rupture and clear the occlusion. In some examples, the distal end 134 of the impactor 130 is between 30 mm and 50 mm, however shorter and longer impactors are also anticipated.

The flexible impactor 130 has material properties that facilitate advancement of the catheter 100 through a body lumen, such as a narrow, tortuous or curved blood vessels or a ureter. The material properties of the flexible impactor 130 are rigid enough to puncture a calcified lesion, such as a CTO cap, when driven into the lesion by a shock wave. The material properties of the impactor 130 are also compliant enough to advance through a lumen without damaging soft tissue of the lumen wall (i.e., the material properties of the impactor 130 may permit the impactor 130 to torque, curve, and bend to navigate through the body lumen). The material of the impactor 130 may include, for instance, a metal (e.g., a stainless steel, a nickel, a titanium, or an alloy thereof). In other examples, the material of the impactor 130 could include a rigid or heat-resistant polymer, e.g., Teflon, parylene. PEEK (Polyether Ether Ketone), or ULTEM (Polyetherimide: PEI). In some examples, the distal tip 135 of the impactor 130 is formed from a more rigid material than a remaining portion of the impactor 130 (e.g., a more rigid material than the material of the distal end 134 or proximal end 132 of the impactor 130). In some examples, the distal tip 135 of the impactor includes a puncturing feature adapted for penetrating a thick fibrous cap of an occlusion, such as a CTO.

Figures 4A, 4B:
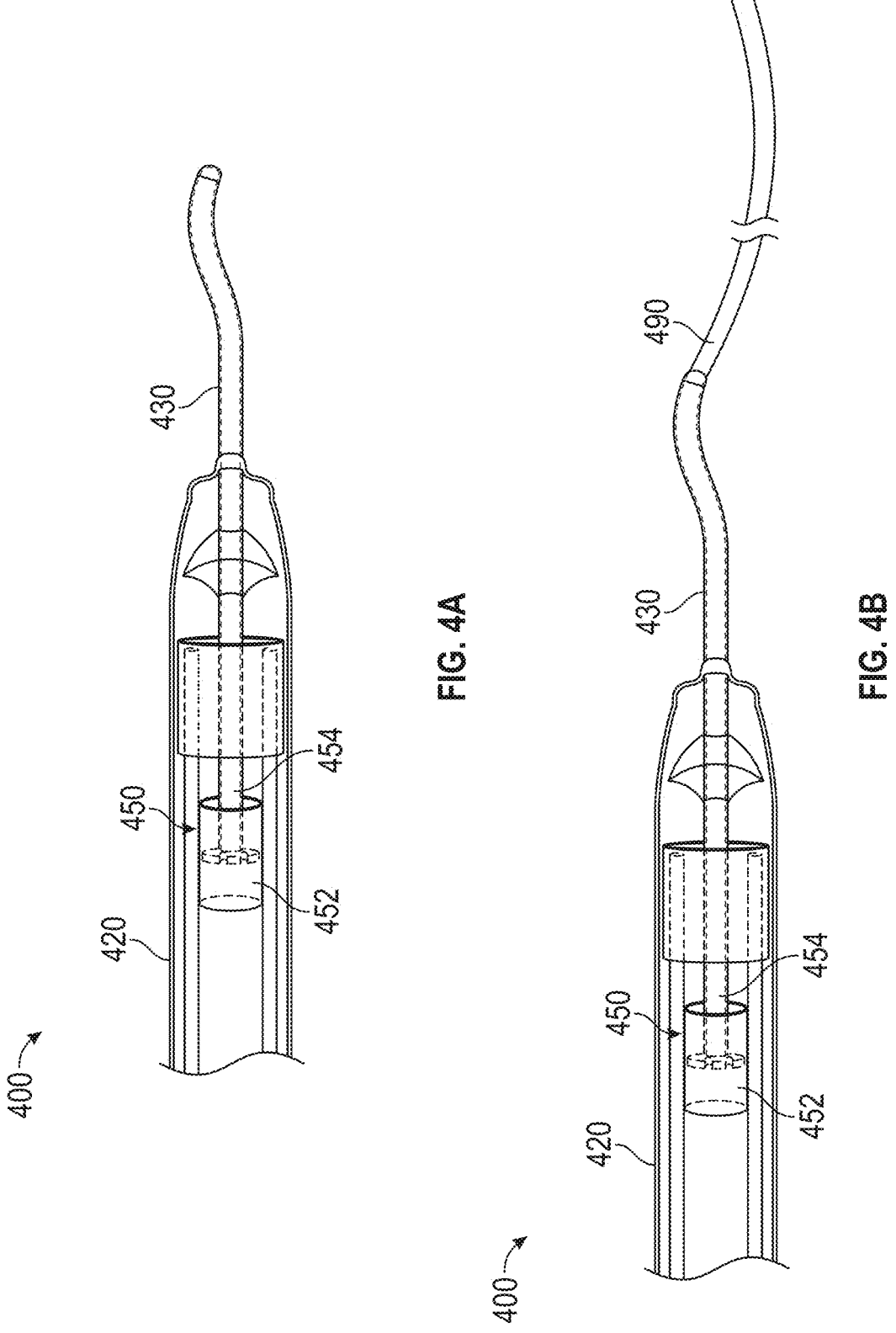
FIG. 4A is an illustration of a catheter having a hollow elongated impactor, according to aspects of the present disclosure.
FIG. 4B is an illustration of the catheter of FIG. 4A with a removable guide wire inserted through the impactor, according to aspects of the present disclosure.

While FIGS. 2-3 illustrate the distal end and impactor 130 of one exemplary catheter 100, an exemplary catheter could be designed with additional or alternative impacting features near the distal end. For instance, FIGS. 4A-4B illustrate another exemplary catheter 400 where the impactor 430 is a hollow elongated flexible member having a longitudinal channel (e.g., a guide wire lumen) for receiving a removable guide wire 490. FIG. 4A shows an exemplary catheter 400 having a hollow elongated impactor 430, and FIG. 4B shows the catheter 400 with a removable guide wire 490 passed through the guide wire lumen of the impactor (e.g., to aid in insertion and advancement of the catheter 400 and/or the removal of the catheter 400 and the insertion of a secondary device).

As shown in FIG. 4A, the impactor 430 could be an elongated hollow member that is bendable or flexible such that the impactor 430 can navigate through curved and complex body lumens. The impactor 430 could be include, for instance, a laser-cut metal tube (e.g., a laser-cut stainless steel or Nitinol tube) or a solid metal tube, but may alternatively be formed of a compliant or semi-compliant polymer. A guide wire lumen extending through the impactor 430 is sized to receive a conventional guide wire. In such examples, a shaft 454 of a centering mechanism 450 (e.g., the centering mechanism 150 described with reference to FIGS. 2-3) may also include a channel (e.g., a guide wire lumen) sized to receive a guide wire. The centering mechanism 450 may also include an O-ring projecting outward between the shaft 454 and the cylinder 452 to prevent the leakage of fluid from the catheter body 420 through the hollow guide wire lumen of the shaft 454 and impactor 430.

Figure 5A:
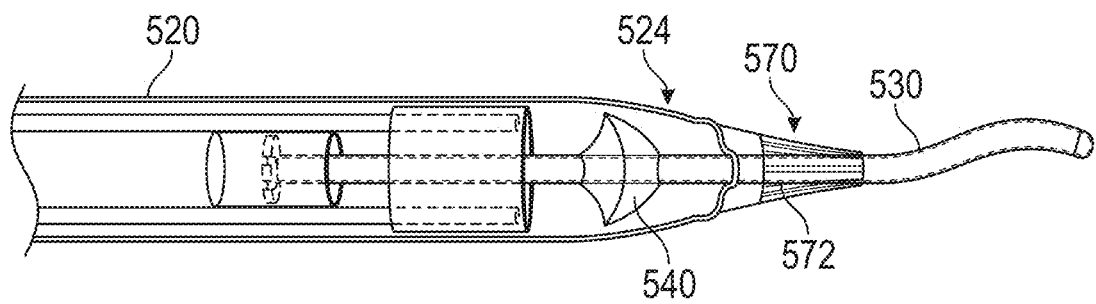
FIG. 5A is an illustration of a distal end of a catheter having a tapered distal tip, according to aspects of the present disclosure.
Figure 5B:
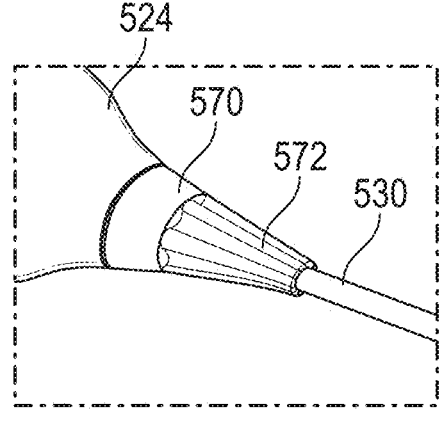
FIG. 5B is a rendering of a tapered distal tip having splines for penetrating an occlusion, according to aspects of the present disclosure.
Figure 5C:
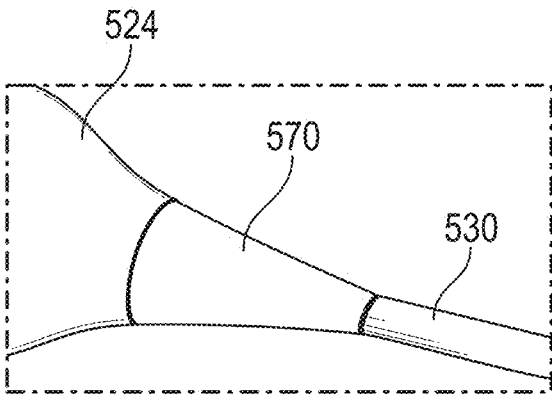
FIG. 5C is a rendering of a tapered distal tip having a smooth outer surface, according to aspects of the present disclosure.

As seen in FIGS. 5A-5C, an exemplary catheter 500 may also include a tapered distal tip 570 coupled to the distal end 524 of the catheter body 520 and surrounding a portion of the impactor 530. The tapered distal tip 570 is configured to oscillate in conjunction with the deflector 540 and impactor 530 to deliver mechanical force to an occlusion, i.e., by advancing forward responsive to the generation of shock waves in the catheter body 520, and advancing backward due to the flexible material properties of the catheter body's distal end 524. FIG. 5A shows the distal end of an exemplary catheter 500 including a tapered distal tip 570 coupled to the distal end of the catheter body. FIGS. 5B and 5C provide renderings of two examples of a tapered distal tips 570 that can be included in an exemplary catheter design.

As shown in FIGS. 5A-5C, an exemplary tapered distal tip 570 may have a substantially conical shape, with an outer surface that tapers between the distal end 524 of the catheter body 520 and the impactor 530. The tapered distal tip 570 also includes a channel (e.g., an impactor lumen) that is sized to fit the impactor 530, such that the impactor passes through and is connected to the distal tip 570. The tapered distal tip 570 may be formed from relatively more rigid material than the flexible and/or inflatable distal end of the catheter body 524. For instance, the tapered distal tip 570 could be formed of a semi-compliant polymer or a rigid polymer. The tapered distal tip 570 may be coupled to the distal end of the catheter body 524 and/or the impactor 530 by way of, e.g., a laser bond or heat seal. As seen in FIGS. 5A-5B, the tapered distal tip 570 may also include penetrating features 572 to facilitate puncturing and crossing of an occlusion in a body lumen, such as a rigid cap of a CTO. The penetrating features 572 could include, for instance, longitudinal splines (e.g., ridges) that extend along the outer surface of the tapered distal tip 570. The penetrating features 572 may cause the tapered distal tip 570 to impact an occlusion with an area of relatively smaller surface area, resulting in a relatively increased mechanical force on the occlusion compared with a distal tip with a smooth outer surface. In other examples, and as seen in FIG. 5C, the outer surface of the tapered distal tip 570 may be smooth.

Returning to FIGS. 2-3, the exemplary catheter 100 also includes a deflector 140 coupled to the proximal end 132 of the impactor 130. The deflector 140 is located between the shock wave source(s) 160 and the distal end 124 of the catheter body 122 and includes a front surface 142 and a back surface 144. As seen in FIGS. 2-3, the front surface 142 of the deflector 140 faces the distal end 124 of the catheter body 120 and is coupled to the impactor 130, while the back surface 144 of the deflector 140 faces the shock wave source 160 and is coupled to a shaft 154 of a centering mechanism 150. When the shock wave source 160 generates a shock wave, at least a portion of the shock wave impinges on the back surface 144 of the deflector 140 causing the deflector 140 to advance in a forward direction (in other words, toward the distal end 124 of the catheter body 120) in conjunction with the impactor 130. In some examples, when the shock wave source 160 generates a shock wave, the deflector 140 advances between 50 µm and 100 µm. However, in other examples the deflector 140 is configured to advance a greater or lesser distance responsive to generation of a shock wave, for instance, between 100 µm and 200 µm, between 200 µm and 500 µm, or less than 50 µm, or at increments and gradients of distance within these ranges.

The deflector 140 projects radially outward from the longitudinal axis of the catheter 100 (e.g., projects outward from the impactor 130 and/or the shaft 154) toward the walls of the catheter body 120. The deflector includes a distal front surface 142 facing toward the distal end 124 of the catheter body 120 and a proximal back surface 144 facing toward the proximal end of the catheter body 120. The deflector 140 may be roughly disk-shaped, or, as seen in FIGS. 2-3, may have a roughly cylindrical shape where the front surface 142 and the back surface 144 are joined at a circumferential edge around the deflector 140. In some examples, the front surface 142 of the deflector 140 is curved or non-linear, e.g., having a convex curved shape. In some examples, the front surface 142 or the back surface 144 of the deflector 140 is shaped to reduce drag caused by forward advancement of the deflector 140 (in other words, to reduce fluid resistance when the deflector 140 oscillates in the conductive fluid within the catheter 120). The back surface 144 of the deflector 140 may also be curved or non-linear, e.g., having a concave curved shape. The diameter of the deflector 140 may be approximately equal to the diameter of the catheter body 120. However, in other examples, the diameter of the deflector 140 is less than the diameter of the catheter body 120 so as to provide a gap between the perimeter of the deflector 140 and the walls of the catheter body 120 (in other words, a gap through which fluid can flow when the deflector 140 oscillates forward and backward within the catheter body 120).

Figure 6:
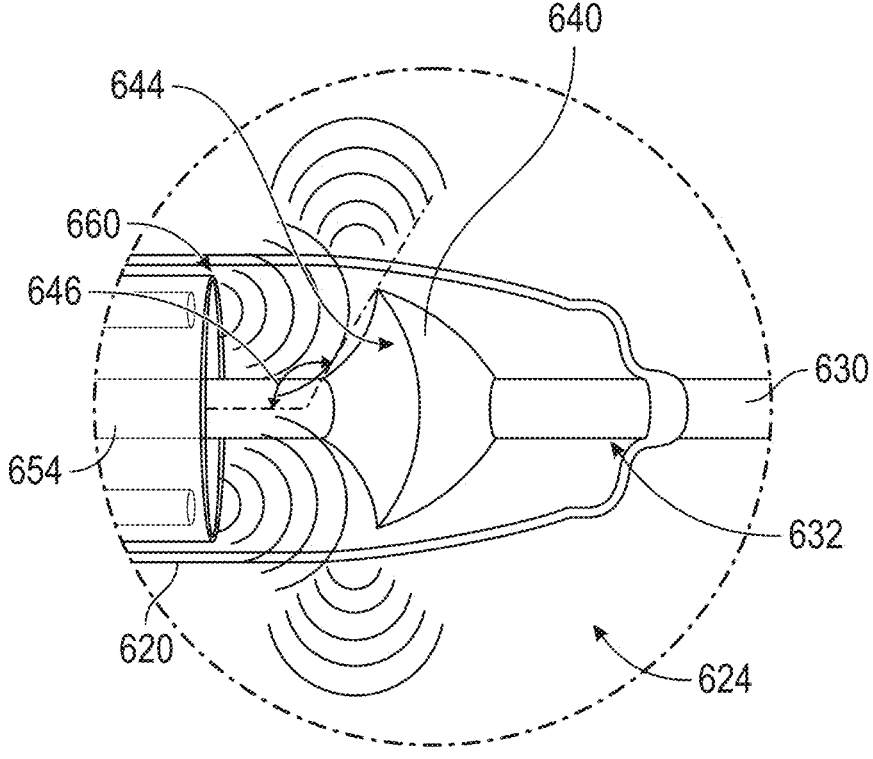
FIG. 6 is an illustration of a catheter generating shock waves to produce mechanical oscillations of a guide wire, according to aspects of the present disclosure.

FIG. 6 provides a perspective sectional view of a distal end of an exemplary catheter 600 showing a deflector 640 deflecting shock waves generated by a shock wave source 660 within the catheter body 620. As seen in FIG. 6, when the shock wave source 660 generates a shock wave, at least a portion of the shock waves impinges on the back surface 644 of the deflector 640. At least a portion of the shock wave that impinges on the back surface 644 of the deflector 640 is deflected in a direction transverse to the catheter 600, in other words, in a direction orthogonal to a central axis of the catheter body 620. In such examples, an initial shock wave may be directed in a forward direction, while a deflected shock wave may be deflected in a direction transverse to the catheter 600. The deflected shock wave energy may propagate through the conductive fluid and through the walls of the distal end 624 of the catheter body 620 to deliver acoustic energy to treat calcified regions of a body lumen surrounding the catheter body 620.

The proportion of the shock wave energy directed to either purpose (i.e., the magnitude of the shock wave energy that causes the deflector 640 to advance in a forward direction compared to the magnitude of the shock wave energy that is deflected in a direction transverse to the catheter body 620) may be determined by a deflector angle 646 between the deflector 640 and the impactor 630. As shown in FIG. 6, the deflector angle 646 is the angle between the longitudinal axis of the catheter 600 (which can be understood as a central longitudinal axis that passes through the axial center of the catheter body 620, the proximal end 632 of the impactor 630, or the shaft 654) and a back surface 644 of the deflector 640. In some cases, e.g., when the back surface 644 of the deflector 640 is non-linear, the deflector angle 646 is the angle between the longitudinal axis of the catheter body 620 and a linear approximation of the back surface 644 of the deflector 640. The deflector angle 646 may be selected to provide a desired magnitude of treatment through either forward advancement of the impactor 630 or transmission of acoustic waves through the walls of the catheter body 620. More specifically, the deflector angle 646 may be selected to provide a first desired proportion of shock wave energy directed to advancing the impactor 630 (i.e., forward shock wave energy), and a second desired proportion of the shock wave energy directed in a direction transverse to the catheter body 620 (i.e., transverse shock wave energy). For instance, a 90 degree deflector angle 646, i.e., an embodiment where the back surface 644 of the deflector 640 projects at a 90 degree angle relative to the longitudinal axis of the catheter body 620, would result in a maximum amount of the shock wave energy to be directed to advancing the impactor 630 (i.e. a maximum amount of forward-directed shock wave energy with little or no energy directed laterally). A deflector angle 646 of approximately 135 degrees, i.e., an embodiment where the back surface 644 of the deflector 640 projects at an obtuse 135 degree angle relative to the longitudinal axis of the catheter body 620, may result in a maximal amount of shock wave energy to be directed in a direction transverse to the catheter (i.e., a maximum amount of transverse shock wave energy). In some examples, the deflector angle 646 between the deflector 640 and the impactor 630 is between 90 degrees and 180 degrees, or at increments or gradients of angle within this range. In further examples, the deflector angle 646 between the deflector 640 and the impactor 630 is between 120 degrees and 150 degrees. In yet further examples, the deflector angle 646 between the deflector 640 and the impactor 630 is approximately 135 degrees.

The deflector 640 may be formed from any desired material, but more preferably is formed from a material that reflect acoustic sound waves. For instance, the deflector 640 could include a rigid material, such as a rigid and/or heat-proof polymer material like PEEK (Polyether Ester Ketone) or ULTEM (Polyetherimide: PEO) or some combination thereof, a metal, or some other rigid or semi-rigid material. In some examples, the deflector 640 is formed from the same material as the flexible impactor 630 or the shaft 654 of the centering mechanism 650. However, in other examples, the deflector 640 is formed from a different material and may be, e.g., laser bonded or heat scaled to the impactor 630 and/or the shaft 654.

Returning to FIGS. 2-3, in some examples the catheter 100 includes a centering mechanism 150 configured to maintain the proximal end 132 of the impactor 130 and the deflector 140 at approximately the axial center of the catheter body 120 (i.e., along the longitudinal axis of the catheter) while permitting forward and backward axial motion of the deflector 140. The centering mechanism 150 may be formed from a cylinder 152 mounted within the catheter body and a shaft 154 mounted to a proximal end of the deflector 140, the shaft 154 being configured to slide within the cylinder 152. When the shock wave source 160 generates a shock wave, the shaft 154 slides forward within the cylinder 152 in conjunction with the deflector 140 and the impactor 130. The shaft 154 optionally includes a spacer 156 that projects outward between the shaft 154 and the walls of the cylinder 152 to retain the shaft 154 at approximately an axial center of the cylinder 152 while permitting forward and backward movement of the shaft 154 along a central axis of the catheter body 120.

The cylinder 152 may be mounted within the catheter body 120 in any desired location. For instance, as seen in FIGS. 2-3, the cylinder 152 may be mounted proximal to the deflector 140 along approximately the central axis of the catheter body 120. However, in other examples the cylinder 152 may be mounted distal to the deflector 140, in other words, mounted in the catheter body 120 between the deflector 140 and the distal end 124. In some examples, the cylinder 152 is mounted in an offset position such that the cylinder 152 is not concentric with the longitudinal axis of the catheter body 120. In some examples, the cylinder 152 is mounted between one or more insulated wires (e.g., a first insulated wire 164 and a second insulated wire 166), and may optionally be coupled to one or more of the insulated wires. In some examples, the catheter body 120 is provided with one or more lumens extending along the length of the catheter body 120, and the centering mechanism 150 includes a shaft 152 configured to slide within a lumen of the catheter body 120.

The shaft 154 is approximately cylindrical and extends from a back surface 144 of the deflector 140 approximately parallel to the longitudinal axis of the catheter body 120. In some examples, the proximal end 132 of the impactor 130 forms the shaft 154 of the centering mechanism 150. In that regard, a length of the impactor 130 may pass through the deflector 140 to provide a shaft 154 that slides within the cylinder 152. In other examples, the shaft 154 may be coupled to the deflector 140 via, e.g., a laser bond, a heat seal, an adhesive, or some other attachment. In some examples, as seen in FIGS. 2-3, the shaft 154 is proximal to the back surface 144 of the deflector 140. However, in other examples the shaft 154 is disposed between the deflector 140 and the distal end 124 of the catheter body 120 (i.e., is coupled to a front surface 142 of the deflector 140 or including a portion of the impactor 130 extending distal to the deflector 140 between the deflector 140 and the distal end 124 of the catheter body 120).

The shaft 154 of the centering mechanism 150 may be sized to loosely slide within the cylinder. For instance, the shaft 154 may have a diameter that is approximately equal to the diameter of the cylinder 152, or a diameter slightly less than a diameter of the cylinder 152, which can thereby provide a gap between the shaft 154 and the cylinder 152 through which fluid can flow while the shaft 154 advances forward and backward within the cylinder 152. Additionally or alternatively, the shaft 154 includes a spacer 156 that projects outward between the shaft 154 and the walls of the cylinder 152. The spacer 156 is adapted to retain the shaft 154 at approximately the center of the cylinder 152, while permitting movement of the shaft 154 along a central axis of the catheter body 120. In some examples, the spacer 156 projects outward from the shaft 154 in a ring shape or a flattened cylindrical shape. In some examples, the spacer 156 includes holes or cut-outs that permit fluid to flow around the spacer 156 when the spacer 156 and shaft 152 advance forward and backward within the cylinder 152, or in other words, when shock waves are generated causing the deflector 140, shaft 154, and spacer 154 to oscillate within the catheter body 120. The cut-outs may be positioned at equal distances around the circumference of the spacer 156. In some examples, the centering mechanism 150 includes two or more spacers 156.

The catheter 100 also includes a shock wave source 160 configured to generate shock waves in the conductive fluid inside the catheter body 120. The distal end 124 of the catheter body 120 surrounds the shock wave source 160 such that shock waves generated at the shock wave source 160 propagate through walls of the catheter body 120 to treat regions of the body lumen proximate to the distal end 124. The shock wave source 160 is positioned proximal to the back surface 144 of the deflector 140 such that, when shock wave source 160 generates a shock wave, at least a portion of the shock wave energy impinges on the deflector 140.

As seen in FIG. 3, repeated shock waves cause the deflector 140 to oscillate forward and backward within the catheter body. The axial oscillation of the deflector causes corresponding axial (i.e., forward and backward) oscillations in the attached impactor 130, producing a "jackhammer" effect that can penetrate an occlusion in a body lumen. The distal tip 135 of the impactor 130, which remains outside the catheter body 120, vibrates responsive to the repeated shock waves at the shock wave source 160 and further disrupts the occlusion. The combination of the "jackhammer" effect and the vibration of the distal tip 135 of the impactor 130 can penetrate a fibrous cap of a CTO and modify calcified regions of a body lumen to restore flow to the body lumen.

In some examples, the shock wave source 160 generates shock waves at a frequency of 10 Hz to 100 Hz (i.e., shock waves are produced at a repetition rate of 10 Hz to 100 Hz), causing the deflector 140 to oscillate at a frequency of about 10 Hz to 100 Hz. In such an example, the impactor 130 may vibrate or "jackhammer" at a frequency of 10 Hz to 100 Hz responsive to the shock waves. However, shock waves may be generated at a higher or lower repetition rate depending on, e.g., the size of the lesion, the extent of calcification, the size of the blood vessel, the attributes of the patient, or the stage of treatment.

As used herein, the shock wave source 160 includes one or more electrode pairs, each electrode pair including a first electrode and a second electrode separated by a gap. Shock waves can be generated at the shock wave source 160 by applying a high voltage pulse across the first and second electrodes of the pair. Each pulse initially ionizes the conductive fluid in the catheter body 120 proximate to the electrodes. At some point, a plasma arc forms across the gap between the electrode pairs, creating a low impedance path where current flows freely. Thermal energy from the plasma arc heats the conductive fluid creating a rapidly expanding vapor bubble. The expansion of the vapor bubble creates an acoustic shock wave that propagates through the conductive fluid inside the catheter body 120.

An electrode pair can be formed from a side edge of a conductive emitter band (e.g., a conductive sheath or a ring electrode) and a conductive portion of a wire, as described in assignee's prior filing U.S. Pub. No. 2019/0150960. The conductive portion of the wire can be formed by removing a portion of the insulating layer of an insulated wire near the distal end of the wire to expose an electrically conductive portion of the wire. The location, size, and shape of the removed portion may vary to control the location, direction, and/or magnitude of the shock wave. In some embodiments, an electrode may be formed by cutting the end of an insulated wire to expose an electrically conductive cross-section, i.e., an exposed distal tip of the wire.

The electrodes pairs may be arranged in a low-profile configuration that reduces the diameter of the distal end 124 of the catheter body 120 to permit the treatment of tighter, harder-to-cross lesions like CTOs. In some examples, the shock wave source 160 includes one or more coplanar electrode pairs, or one or more electrodes at least partially surrounded by a conductive emitter band. In some embodiments, flat wires rather than round wires are used to further reduce the crossing profile of the electrode assembly.

The assignee herein has developed a number of low-profile shock wave electrodes that may be suitable for use in a catheter for treating occlusions, such as CTOs. For example, in U.S. Pub. No. 2019/0150960, the assignee discloses a low-profile electrode assembly, in which an outer electrode is formed by a conductive sheath, and an inner electrode is formed by a conductive portion of an insulated wire (e.g., an exposed distal tip of the wire, or an insulation-removed portion of the wire formed from removing a layer of insulation from the wire). The inner electrode is placed a controlled distance apart from the side edge of the conductive sheath to allow for a reproducible arc for a given current and voltage.

More recently, the assignee has developed a number of coplanar electrode assemblies for use in catheters. Various coplanar electrode configurations are described in U.S. Pat. Nos. 8,888,788; 10,966,737; 10,555,744; and U.S. Pub. No. 2019/0150960, incorporated herein by reference. These designs provide novel configurations of electrode pairs having, e.g., helical structures and tongue-and-groove designs, with respective electrodes on the same lateral plane to limit the overall thickness of the electrode assemblies. These assemblies are particularly advantageous for generating shock waves in tight, hard-to-pass lesions or totally occluded vasculature. For example, in U.S. Pat. No. 9,993, 292 and U.S. Publication No. 2018/0098779, incorporated herein by reference, the assignee discloses forming electrode pairs from helically wound wires to generate shock waves at various gaps positioned circumferentially around a tubular structure. In U.S. Pat. No. 10,555,744, also incorporated herein by reference, the assignee discloses a tongue-andgroove electrode assembly in which electrode pairs are formed from a groove-shaped cut-out in a conductive sheath and a coplanar tongue-shaped protrusion extending into the groove-shaped cut-out.

Returning to FIGS. 2-3, an exemplary catheter 100 includes a first insulated wire 164 extending along the length of the catheter 100, a second insulated wire 166 extending along the length of the catheter 100, and a conductive emitter band 162 mounted within the catheter 100. Each of the first and second insulated wires 164, 166 can be an insulated wire, where the conductive metal can be copper, aluminum, stainless steel, molybdenum, tungsten, or a combination thereof. Each of the first and second insulated wires 164, 166 includes an uninsulated conductive portion, such as an exposed distal tip of the wire, that functions as a first electrode of an electrode pair.

The conductive emitter band 162 surrounds the exposed distal tips of the first and second insulated wires 164, 166 and functions as a second electrode of the electrode pairs. The conductive emitter band is mounted within the interior volume of the catheter body 120 and circumscribes the ends of the two insulated wires 164, 166 without contacting the wires. The conductive emitter band 162 may be a conductive cylinder, for instance, a metal cylinder including stainless steel, tungsten, platinum, iridium, or an alloy thereof. In some examples, the emitter band 162 is mounted in the catheter body 120 at a position more distal than the exposed distal tips of the first insulated wire 164 and the second insulated wire 166 to encourage the shock waves to propagate in a substantially forward direction (e.g., toward the back surface 144 of the deflector 140 and the distal end 124 of the catheter body 120).

In such an example, and as depicted in FIGS. 2-3, the shock wave source 160 includes two electrode pairs, the electrodes of each respective pair being formed from the conductive portions of the insulated wires 164, 166 and the conductive emitter band 162 mounted within the catheter body 120. More specifically, the shock wave source 160 may include a first electrode pair, the first electrode pair including a first electrode formed from the exposed distal tip of the first insulated wire 164 and a second electrode formed from the conductive emitter band 162. The shock wave source 160 may further include a second electrode pair, the second electrode pair including a first electrode formed from the exposed distal tip of the second insulated wire 166 and a second electrode formed from the conductive emitter band 162.

The catheter 100 also includes a voltage source (e.g., the generator 28 depicted in FIG. 1) configured to deliver high voltage pulses across the shock wave source 160. When a high voltage pulse is applied across the first insulated wire 164 and the second insulated wire 166, a current is configured to flow from the exposed distal tip of the first insulated wire 164 to the conductive emitter band 162 to generate a first shock wave across the first electrode pair. The current is further configured to flow from the conductive emitter band 162 to the exposed distal tip of the second insulated wire 166 to generate a second shock wave across the second electrode pair. In some examples, the voltage source is configured to deliver high voltage pulses at a voltage between 100 V and 3,000 V, or more specifically between 2,300 V and 3,000 V. In further implementations, the voltage source can be configured to deliver high voltage pulses at a voltage between 100 V and 10,000 V, and at increments or gradients of voltage within that range. Further, the voltage source may be configured to deliver the high voltage pulses at a desired repetition rate, for instance, at a rate of 10 Hz to 100 Hz. However, the voltage source can be configured to deliver voltage pulses across the shock wave source 160 at any desired voltage and repetition rate. In some examples, the voltage source may be controlled by a physician during treatment to deliver, when desired, a higher or lower voltage pulse, or a higher or lower repetition rate of the voltage pulses. For instance, a physician may start with low energy shock waves and increase the energy as needed during treatment. Alternatively, a physician may start with high energy shock waves, e.g., to rupture a fibrous CTO cap with the impactor 130, and may decrease the energy as needed during the remainder of the treatment. The magnitude of the shock waves can be modified by controlling the voltage, current, duration, and repetition rate of the pulsed voltage from the pulsed voltage source. More information about the physics of shock wave generation and their control can be found in U.S. Pat. Nos. 8,956,371; 8,728,091; 9,522,012; and 10,226,265, each of which is incorporated by reference.

In some examples, the catheter 100 includes an insulating sheath (e.g., a polyimide insulated ring) mounted within the catheter body 120 between the conductive emitter band 162 and the exposed distal tips of the insulated wires 164, 166. The insulating sheath may be mounted concentric and internal to the conductive emitter band 162 and may be adapted to prevent accidental current flow and leaks between electrodes in the catheter body 120 (e.g., between conductive portions of the insulated wires 164, 166 and the conductive emitter band 162). The insulating sheath may include holes located between electrodes of the respective electrode pairs, such that the insulating sheath provides paths for current to flow between the conductive emitter band 162 and the conductive portions of the insulated wires 164, 166, the paths flowing through the holes of the insulating sheath.

The placement and spacing of the electrode pairs (e.g., the conductive emitter band(s) 162 and the insulated wires 164, 166) can be controlled to provide a more effective shock wave treatment. For instance, the electrode pairs of the shock wave source 160 may be spaced circumferentially inside the distal end 124 of the catheter body 120 in consistent increments, e.g., 180 degrees apart or 90 degrees apart, to generate shock waves more evenly around the catheter 100. For instance, while the catheter shown in FIGS. 2-3 includes a first insulated wire 164 and a second insulated wire 166, a catheter 100 could have more than two wires, and could be configured to generate shock waves at more than two pairs of electrodes. In a particular example, the catheter may include a second pair of insulated wires (not shown) offset from the first and second insulated wires 164, 166 by 90 degrees. For example, if the first and second insulated wires 164, 166 are positioned at 0 and 180 degrees, a third and fourth insulated wire may be positioned at 90 and 270 degrees. The third and fourth insulated wires also end near the distal end of the catheter body and include conductive exposed distal tips that function as electrodes. A conductive emitter band (e.g., the conductive emitter band 162 or a further emitter band) circumscribes the exposed distal tips of the third and fourth insulated wires, and a separate high voltage pulse may be applied across the third and fourth insulated wires to generate a second pair of shock waves between the insulated wires and the emitter band. As a result, a second set of shock waves may be initiated from a third and fourth electrode pair of the catheter formed from a conductive emitter band and conductive portions of third and fourth insulated wires. The first pair of insulated wires (i.e., the first insulated wire 164 and the second insulated wire 166) and the second pair of insulated wires (i.e., the third insulated wire and the fourth insulated wire) may be activated alternately, which may improve the effectiveness of the device by further spreading the shock waves around the circumference of the catheter.

In some embodiments, the shock wave source 160 includes electrode pairs positioned in various groupings spaced longitudinally inside the catheter body 120. For example, to generate shock waves at more medial locations in the catheter body 120, i.e., in order to advantageously treat a larger area of a body lumen surrounding the catheter body 120, the catheter 100 may include one or more medial shock wave sources. A distal shock wave source (e.g., the shock wave source 160) could be configured to generate shock waves to advance the deflector 140 and the impactor 130 to treat occlusions distal to the catheter body 120 (with a portion of the shock wave energy also directed in a direction transverse to the catheter 100 to treat regions of a body lumen surrounding the distal end 124 catheter body 120), while medial shock wave sources could be configured to generate shock waves to treat regions of the body lumen surrounding a medial portion of the catheter body 120. In some examples, the catheter 100 includes a secondary conductive emitter band mounted in a medial location of the catheter body 120 (e.g., at a location proximal to the conductive emitter band 162), as well as an associated pair of insulated wires (e.g., the third and fourth insulated wires described above) spaced from the secondary emitter band to form respective first and second medial electrode pairs for generating shock waves. When a high voltage pulse is applied across the third insulated wire and the fourth insulated wire, a current is configured to flow from the exposed distal tip of the third insulated wire to the secondary conductive emitter band to generate a first medial shock wave across the first medial electrode pair. The current is further configured to flow from the secondary conductive emitter band to the exposed distal tip of the fourth insulated wire to generate a second medial shock wave across the second electrode medial pair.

Any number of conductive emitter bands may be used to generate shock waves at various locations along the length of the catheter body 120. For instance, in some examples the catheter 100 includes three, four, or five conductive emitter bands spaced along the length of the catheter body 120, as well as associated pairs of insulated wires spaced from the respective bands to form respective electrode pairs for generating shock waves. In some examples, the secondary or further emitter bands may generate shock waves independently of the emitter band at the distal end of the device.

All of the above discussed shock wave sources include electrode pairs and a high voltage source for generating electrohydraulic shock waves across the gap between the electrodes. It is also within the scope of the subject invention to utilize other types of shock wave sources. For example, it is well known that focused laser light can generate a shock wave in a fluid. The laser light can be delivered from an external laser device into the catheter body via an optical fiber. The optical fiber can extend down the catheter in a lumen similar to the wires 164 or 166. In operation, pulses of high energy laser light are injected into the proximal end of the optical fiber and delivered out the distal end of the fiber. The distal end of the fiber would be located in the region behind the deflector 140. The pulse of would vaporize the fluid creating a shock wave that would impact on surface 144 of deflector 140. In use, pulses of laser light would be generated creating a series of shock waves to cause the guidewire to oscillate and jackhammer the occlusion. Lasers with high saline or water absorption coefficients are of particular interest because they generate more effective shockwaves. A high absorption coefficient corresponds to a shallow absorption depth, so the laser energy is confined to a small depth in the liquid and hence heats and vaporizes it very rapidly. Examples of preferred lasers include Ho:YAG (2120 nm), Tm:YAG (2010 nm), Tm fiber laser (1940 nm) and Er:YAG (2940 nm).

FIG. 7 is a flowchart representation of an exemplary method 700 for treating an occlusion in a body lumen, such as a kidney stone in a patient's ureter or a CTO or circumferential calcium in a patient's blood vessel. As depicted in FIG. 7, a catheter is introduced into a patient's body lumen (702), such as a blood vessel in a patient's vascular system or a ureter in a patient's urinary system. The catheter may be any of the catheters described herein in reference to in FIG. 1-3, 4A-4B, 5A-5C, 6, 8, 9A, or 10A. More particularly, the catheter includes at least a catheter body having a distal end, the catheter body being fillable with a conductive fluid; a impactor connected to the distal end of the catheter body, the impactor having a proximal end inside the catheter body and a distal end outside the catheter body; a shock wave source configured to generate a shock wave; and a deflector coupled to the proximal end of the impactor in between the shock wave source and distal end of the catheter body.

In operation, a physician may introduce the catheter into a patient's body lumen by first inserting the impactor into an entry site on a patient (e.g., an artery in the groin area of the leg) and then maneuvering the catheter body and the handle to advance the catheter through the lumen to the target treatment region (e.g., a region having an occlusion that needs to be ruptured to restore flow to the lumen). Additionally or alternatively, e.g., in examples where the impactor includes a guide wire lumen, a physician may first insert a removable guide wire through the guide wire lumen and into the body lumen. The physician may then advance the catheter into the body lumen over the removable guide wire and toward the target treatment region.

The catheter is then advanced within the body lumen such that a distal end of a impactor is positioned proximate to an occlusion in a body lumen (704). In some examples, as seen in FIG. 1, the catheter may be advanced until the distal end of the impactor abuts against an occlusion or is at least partially inside an occlusion. Additionally or alternatively, the catheter may be advanced until the distal end of the catheter body is positioned proximate to a calcified region of the lumen (i.e., to deliver shock wave treatments through the walls of the catheter body). If the catheter has been advanced over a removable guide wire, the physician may then optionally remove the guide wire. However, in other examples the physician may retain the removable guide wire inside the catheter during treatment (e.g., retain the guide wire inside the lumen of the impactor and/or flush with the distal tip of the impactor to prevent debris and tissue from entering the impactor).

The catheter body is then filled with conductive fluid (e.g., saline or saline mixed with a contrast agent) such that the fluid covers the shock wave source (e.g., one or more electrodes). In some cases, the catheter is filled until the conductive fluid at least partially inflates the catheter body. Once the distal end of the impactor is positioned proximate to an occlusion and the catheter body is filled with conductive fluid, a series of shock waves can be generated inside the catheter body (706). The series of shock waves impinge on the deflector causing the deflector to advance in a forward direction in conjunction with the impactor such that the distal end of the impactor delivers a mechanical force to the occlusion for each generated shock wave. In some examples, the shock wave source includes one or more electrode pairs, and generating the series of shock waves includes applying a high voltage pulse across the one or more electrode pairs. In another example, the shock wave source is a laser, and generating the series of shock waves includes using the laser to deliver high energy pulses of laser light. Between each shock wave of the series, the flexible material properties of the distal end of the catheter body cause the impactor and the deflector to return backward to their original position in the catheter body. As described above, repeated shock waves cause the impactor to oscillate and vibrate to penetrate and clear an occlusion and restore flow to a body lumen.

Repeated advancement of the catheter through a target region of a body lumen and application of repeated shock wave cycles can clear even rigid and chronically occluded regions of a body lumen. For instance, in some examples, the method further includes advancing the catheter further within the body lumen such that the distal tip of the impactor is proximate to a further treatment region, e.g., a more distal occluded area of a CTO or a more distal region of vasculature that is a calcified or partially occluded. The method may then include generating a further series of shock waves. As described above with reference to FIGS. 5A-5C, in some examples the catheter includes a tapered distal tip that is configured to advance in conjunction with the impactor and deflector in response to the generation of shock waves. The tapered distal tip can be used to deliver mechanical forces to portions of an occlusion more proximate to the catheter body (i.e., at a more proximal region of the lumen compared to the distal tip of the impactor) to continue to penetrate and clear an occlusion. In such examples, the method may include advancing the catheter further within the body lumen such that the tapered distal tip is positioned proximate to a treatment region (708), e.g., a treatment region previously penetrated by the impactor. The method may then include generating a further series of shock waves (710) to advance the tapered distal tip into an occlusion.

In one or more examples, after generating a further series of shock waves to advance the tapered distal tip into an occlusion (708), the method 700 can again advance the catheter further within the body lumen such that the tapered distal tip is proximate to a further treatment region (710) before again generating a further series of shock waves (710). That is, in one or more examples, after step 710, the method 700 can repeat step 708 and then step 710 in a loop. Optionally, this loop of repeating steps 708 and 710 can be repeated multiple times.

To eliminate the need for multiple devices during treatment of an occlusion, the same catheter may be used to modify calcified and partially occluded regions proximate to the catheter body by delivering acoustic shock wave energy through walls of the catheter body (e.g., transverse shock waves). For instance, after modifying a totally or partially occluded region of a lumen using impacts from the distal tip of the impactor, the method 700 may further include advancing the catheter further within the body lumen such that the catheter body is positioned proximate to a transversely located treatment region (712) (e.g., to an occlusion previously penetrated by the impactor or some other calcified or partially occluded region). After advancing the catheter further within the body lumen, the method may include generating transversely directed shock waves (714) to deliver acoustic shock wave energy to a transversely located occlusion. The transverse shock wave energy can propagate through walls of the catheter body to treat regions of a body lumen proximal to the catheter body. In one or more examples, when advancing the catheter such that the body of the catheter is proximate to a transversely located treatment region at step 712, the distal tip may also be proximate to a further treatment region. In such case, when generating transversely directed shock waves at step 714, in addition to transmitting shock wave energy in a direction transverse to the catheter, at least a portion of the shock wave energy may be transmitted to produce oscillations that advance the distal end of the impactor.

In one or more examples, after generating transversely directed shock waves at step 714, the method 700 can again advance the catheter further within the body lumen such that the body of the catheter is proximate to a transversely located treatment region (714) before again generating transversely directed shock waves (714). That is, in one or more examples, after step 714, the method 700 can repeat step 712 and then step 714 in a loop. Optionally, this loop of repeating steps 712 and 714 can be repeated multiple times.

In some examples, treating an occlusion in a body lumen could include one or more treatment stages. For instance, during initial treatment of a tight or totally-occluded region of a lumen, a first treatment stage could include penetrating the occlusion with the distal tip of the impactor to restore flow in the lumen. Once the occluded region is wide enough to permit passage of the catheter body, the catheter body can be advanced further into the occluded region. During a second and subsequent treatment stage, additional shock waves can be generated to deliver additional shock wave energy to regions of the lumen surrounding the catheter body. The voltage and repetition rate of the shock waves may be modified during various treatment stages by a physician, as needed.

Where the catheter includes more than one shock wave generator (e.g., a distal and a medial electrode pair), a first treatment stage could include generating shock waves at a first (e.g., a distal) electrode pair, and a second treatment stage could include generating shock waves at a second (e.g., a proximal) electrode pair. In a first stage of treatment, only the distal electrode pairs may generate shock waves to cause the impactor to advance forward to deliver a mechanical force to an occlusion in a body lumen. After the occlusion has been modified (e.g., the rigid CTO cap has been penetrated by the distal tip of the impactor), the catheter may be advanced further into the occlusion and additional electrode pairs can be activated to generate more medial shock waves.

In other examples, the catheter may be removed from the body lumen and replaced with a secondary device to continue treatment. The secondary device may be inserted and advanced into a target region of a body lumen over a guide wire (e.g., the removable guide wire described above or a further guide wire).

Figure 8:
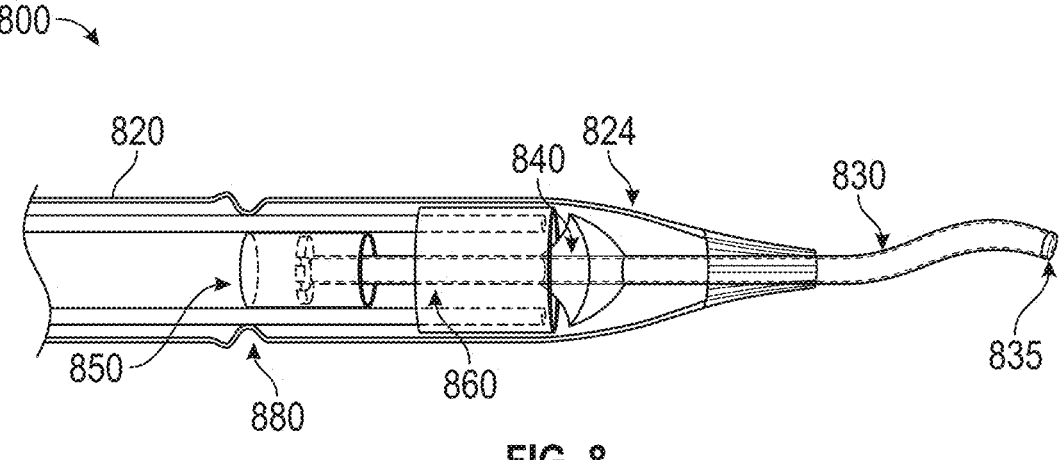
FIG. 8 is an illustration of a distal end of a catheter having a tapered distal tip and a bellows, according to aspects of the present disclosure.

FIG. 8 illustrates an exemplary catheter 800 with a bellows 880 for treating an occlusion in a body lumen, such as the catheter described in relation to FIG. 1. Similar to the catheters described above and as shown in FIG. 8, the catheter 800 includes a deflector 840, a centering mechanism 850, a catheter body 820, a flexible impactor 830, and a shock wave source 860 that are can be configured as discussed above.

As shown in FIG. 8, the catheter 800 includes a bellows 880 located on the walls of the catheter body 820. In some embodiments, the bellows 880 can be formed from concertinaed portions of the wall of the catheter body 820 that provide an axial cushion enabling a front portion of the catheter body 820 to axially translate (e.g., rightward and leftward). In some embodiments, the bellows 880 can enable the catheter body 820 to stretch to a stretched position by flattening the bellows 880, and to return to an unstretched position wherein the bellows 880 are positioned in a folded manner. Accordingly, in some embodiments, the bellows 880 can permit the distal end 824 of the catheter body 820, and more specifically, the portion of the catheter body 820 that is located between the distal end 824 and the bellows 880, to move in a forward direction when the bellows 880 are stretched. In some embodiments, the portion of the catheter body 820 that is located between the proximal end of the catheter 800 and the bellows 880 will remain static while the portion of the catheter body 820 located between the bellows 880 and the distal end 824 moves. In some embodiments, the bellows 880 can be formed from a flexible or semi-compliant material that enables the folds of the bellows 880 to stretch and flatten as discussed above.

The shock wave source 860 of the catheter 800 can be configured like the shock wave sources discussed above. For instance, the shock wave source 860 can be configured to generate shock waves in conductive fluid inside the catheter body 820 that propagate through walls of the catheter body 820 to treat regions of the body lumen proximate to the distal end 824 of the catheter 800. As discussed above, the generation of repeated shock waves by the shock wave source 860 can cause the deflector 840 to oscillate forward and backward within the catheter body 820. Furthermore, the axial oscillation of the deflector 840 can cause corresponding axial (i.e., forward and backward) oscillations in the attached impactor 830, producing a "jackhammer" effect that can penetrate an occlusion in a body lumen. The distal tip 835 of the impactor 830 can vibrate responsive to the repeated shock waves from the shock wave source 860, further disrupting the occlusion. In some embodiments, both the distal tip 835 of the impactor 830 and the portion of the catheter between the bellows 880 and the distal end 824 can vibrate responsive to the repeated shock waves from the shock wave source 860. The "jackhammer" effect and/or the vibration of the distal tip 835 and/or the vibrating portion of the catheter 800 can penetrate a fibrous cap of a CTO and modify calcified regions of a body lumen to restore flow to the body lumen.

The shock wave source 860 can include one or more electrode pairs, with each electrode pair including a first electrode and a second electrode separated by a gap. As discussed above and as shown in FIG. 8, the electrode pair of the shock wave source 860 is formed from a side edge of a conductive emitter band (e.g., a conductive sheath or a ring electrode) and a conductive portion of a wire.

Alternative electrode configurations are suitable for use in a catheter according to the present invention. For instance, the catheter 900 depicted in FIG. 9A, relies on a shockwave source 960 with a coaxial emitter. The catheter 900 can otherwise be configured similarly to the catheter 800 discussed above. The coaxial emitter of the shock wave source 960 can be formed from an outer conductive sheath mounted circumferentially around and concentric with an inner conductive sheath each connected to an insulated wire.

An exemplary coaxial emitter shock wave source, such as the shock wave source 960 of the catheter 900, is shown in FIG. 9B. The shock wave source 960 includes a first cylindrical conductive sheath configured as an inner conductive sheath 930 and a second cylindrical conductive sheath configured as an outer conductive sheath 922. The outer conductive sheath 922 is mounted circumferentially around and concentric with the inner conductive sheath 930, such that the inner and outer conductive sheaths form respective inner and outer electrodes of an electrode pair.

The conductive sheaths 930, 922 are formed from a conductive material, such as a conductive metal, that has been shaped into an extended tubular or cylindrical shape. In some examples, the inner conductive sheath 930 and/or outer conductive sheath 922 are formed from an erosion resistant metal tubing, such as stainless steel, platinum, iridium, molybdenum, tungsten, or copper tubing. The inner conductive sheath 930 may be any desired thickness, for example, between 0.002 and 0.003 inches thick. The outer conductive sheath 922 may be relatively thicker than the inner conductive sheath. For instance, the outer conductive sheath 922 could be approximately 0.004 to 0.006 inches thick. However, in other examples the inner conductive sheath 930 is thicker than the outer conductive sheath 922. For instance, the inner conductive sheath 930 could be between 0.004 to 0.006 inches thick, and the outer conductive sheath 922 could be relatively thinner, e.g., between 0.002 and 0.003 inches thick.

The inner conductive sheath 930 and the outer conductive sheath 922 each include a respective distal side edge 931, 923. The distal side edge 931 of the inner conductive sheath 930 is positioned proximate to the distal side edge 923 of the outer conductive sheath 922 to provide an arcing region between the sheaths across which current can flow to generate a shock wave inside the catheter. Together, the distal side edge 931 of the inner conductive sheath 930 and the distal side edge 923 of the outer conductive sheath 922 form an electrode pair of the electrode assembly. As will be described in more detail below, the distal side edge 931 of the inner conductive sheath 930 may be shaped such that a particular portion of the distal side edge 931 (e.g., portion 925) is closer to the outer conductive sheath 922 than the remainder of the distal side edge (i.e., to provide a predetermined initial arcing region between the conductive sheaths).

As seen in FIG. 9B, the inner conductive sheath 930 and the outer conductive sheath 922 are separated by a cylindrical insulating layer 942, e.g., an insulation sheath, mounted between and concentric with the conductive sheaths 930, 922. The insulating layer 942 is formed from a non-conductive insulating material that prevents unintended current flow between the inner surface of the outer conductive sheath 922 and the outer surface of the inner conductive sheath 930. In some examples, the insulating layer 942 is formed from a polymeric material, e.g., a polyimide, shaped into an extended tubular or cylindrical shape. In some examples, the insulating layer 942 is approximately 0.002 to 0.004 inches thick. As seen in FIG. 1, the insulating layer 942 has a distal side edge that is proximate to (e.g., flush with) the distal side edges 931, 923 of the respective inner and outer conductive sheaths 930, 922. The proximal side edge of the insulating layer extends beyond the proximal side edge of at least one of the inner conductive sheath 930 and/or the outer conductive sheath 922 to prevent unintended current flow between the proximal side edges of the conductive sheaths 930, 922. The shape and position of the insulation layer 942 ensures that the initial arcing region between the inner conductive sheath 930 and outer conductive sheath 922 (i.e., the path of least resistance for current flow, normally the closest-distance location between the sheaths) is between the respective distal side edges 931, 923, and more particularly at the flush portion 925 of the inner conductive sheath 930.

In some examples, the distal side edge 931 of the inner conductive sheath 930 is shaped to have various regions that are closer or farther away from the paired distal side edge 923 of the outer conductive sheath 922, i.e., to promote degradation in a predefined or semi-controlled manner. For instance, the distal side edge 931 of the inner conductive sheath 930 could be shaped such that a portion 925 of the distal side edge 931 is closest to the distal side edge 923 of the outer conductive sheath 922, i.e., in order to provide a predetermined initial arcing region for current flow between the conductive sheaths 930, 922. Second and further arcing regions could be provided by shaping additional portions of the distal side edge 931 to be the second closest to the distal side edge 923, and so on.

As shown in FIG. 9B, the electrode shock wave source 960 also includes two insulated wires 966, 964 extending along the length of the catheter. More particularly, a first insulated wire 966 is electrically connected with the inner conductive sheath 930 and a second insulated wire 964 is electrically connected with the outer conductive sheath 922. The insulated wires 966, 964 provide an electrical connection between the conductive sheaths 930, 922 and an external voltage source, e.g., a high voltage pulse generator (not pictured). In some examples, the inner conductive sheath 930 is connected to a positive terminal of the voltage source, and the outer conductive sheath 922 is connected to a negative terminal of the voltage source or to ground. However, the reverse connection is also envisioned (i.e., with the outer conductive sheath 922 connected to a positive terminal, and the inner conductive sheath connected to a negative terminal or to ground). In some examples, the conductive portions of the wires 966, 964 are heat-sealed or otherwise fixed to the conductive sheaths 930, 922 to provide a direct electrical connection. The insulated wires 966, 964 may extend within a fluid lumen of the catheter, e.g., fixed to a side wall of the lumen or disposed within grooves extending along the lumen. In other examples, the wires 966, 964 extend through a separate lumen of the catheter, e.g., a wire lumen.

A series of high voltage pulses can be delivered across the wires 966, 964 by an external voltage source, e.g., a pulsed high voltage source, to generate a series of shock waves at the electrode shock wave source 960. Negative and positive terminals of the external voltage source are connected to the proximal ends of the first insulated wire 964 and the second insulated wire 964, creating a potential difference across the inner conductive sheath 930 and the outer conductive sheath 922 (i.e., an electrode pair of the electrode assembly) when high voltage pulses are delivered across the wires 966, 964. The potential difference causes current to flow through the electrode pair to generate shock waves. The direction of current flow is dependent on the polarity of the electrodes, with current flowing from the more positively charged electrode (i.e., the electrode that is connected to the positive terminal of the voltage source) to the more negatively charged electrode (i.e., the electrode that is connected to the negative terminal of the voltage source). The duration and magnitude of the voltage pulse is sufficient to generate a gas bubble on the surface of the electrodes (i.e., on the distal side edges 931, 923 of the conductive sheaths 930, 922) and/or a shock wave.

Figure 10A:
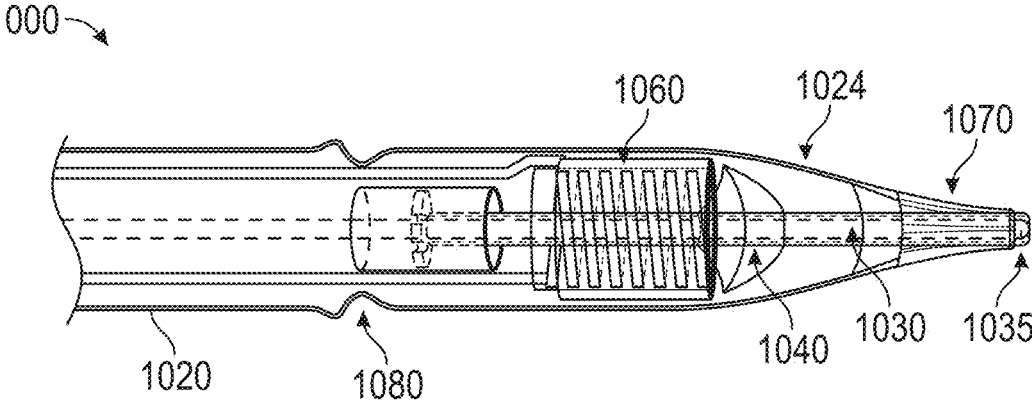
FIG. 10A is an illustration of a distal end of a catheter having a rigid tapered distal tip and a flat wire emitter, according to aspects of the present disclosure.
Figure 10B:
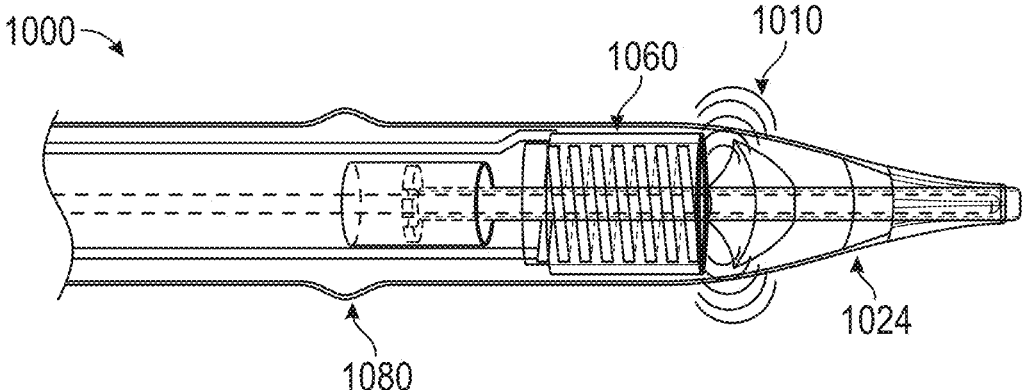
FIG. 10B is an illustration of the distal end of the catheter of FIG. 10A generating shock waves that impinge on a deflector, according to aspects of the present disclosure.

Another electrode configuration is shown in FIGS. 10A-B, which illustrate the distal end of a catheter 1000 having a bellows 1080, a rigid tapered distal tip 1030, and shock wave source 1060 comprising a flat wire emitter within a conductive sheath. Specifically, FIG. 10A depicts the distal tip of the catheter 1000, while FIG. 10B depicts the distal tip of the catheter 1000 while generating shock waves 1010 via the shock wave generator 1060.

According to an embodiment, the catheter 1000 can include a centering mechanism, a deflector 1040, and a catheter body 1020 with bellows 1080 as discussed above, with the shock wave source 1060 configured to similarly generate shock waves that impinge on a back side of the deflector 1040. As shown in FIG. 10A, the deflector 1040 is connected to an impactor 1030 that is located inside the catheter body 1020, and extends from the deflector 1040 to the rigid tip 1070 of the catheter 1000. The rigid tip 1070 can be tapered in various manners, as discussed above. Rather than extend outwardly on the exterior of the catheter body 1020, the distal tip 1035 of the impactor 1030 is located proximate to the rigid tip 1070 of the catheter 1000.

As shown in FIG. 10A, when the shock wave source 1060 of the catheter 1000 is not generating shock waves, the bellows 1080 of the catheter can be in a folded unstretched position. When the shock wave source 1060 is generating shock waves, however, the bellows 1080 can flatten, thereby permitting the portion of the catheter 1000 located between the distal end 1024 of the catheter 1000 and the bellows 1080 to move in a forward direction. According to an embodiment, this portion of the catheter 1000 that is located forward of the bellows 1080 can be configured to vibrate in an axial direction (e.g., forward and backward) as a result of the shock waves impinging on the deflector 1040. As discussed above, in some embodiments, the portion of the catheter body 1020 that is located between the proximal end of the catheter 1000 and the bellows 1080 will remain static while the portion of the catheter body 1020 located between the bellows 1080 and the distal end 1024 moves.

In one or more examples, the impactor 1030 can be configured to translate axially in response to shock waves generated via the shock wave generator 1060. The axial oscillation of the deflector 1040 can cause corresponding axial (i.e., forward and backward) oscillations in the attached impactor 1030, producing a "jackhammer" effect that can penetrate an occlusion in a body lumen. The distal tip 1035 of the impactor 1030 can vibrate responsive to the repeated shock waves from the shock wave source 1060, further disrupting the occlusion. In some embodiments, both the distal tip 1035 of the impactor 1030 and the portion of the catheter between the bellows 1080 and the distal end 1024 can vibrate responsive to the repeated shock waves from the shock wave source 1060. The "jackhammer" effect and/or the vibration of the distal tip 1035 and/or the vibrating portion of the catheter body can penetrate a fibrous cap of a CTO and modify calcified regions of a body lumen to restore flow to the body lumen. As discussed above, in addition to the "jackhammer" effect of the impactor 1030, at least a portion of the shock waves generated via the shock wave source 1060 can be deflected by the back surface of the deflector 1040 in a direction that is transverse to the catheter 1000. Thus, the catheter 1000 can be configured to harness both the "jackhammer" effect of the impactor 1030 and/or the vibrating portion of the catheter body to break up occlusions proximate to the distal tip 1035 of the impactor 1030 and the transversely propagated shock waves to break up occlusions proximate to the body 1020 of the catheter 1000, as will be discussed further below.

Figure 10C:
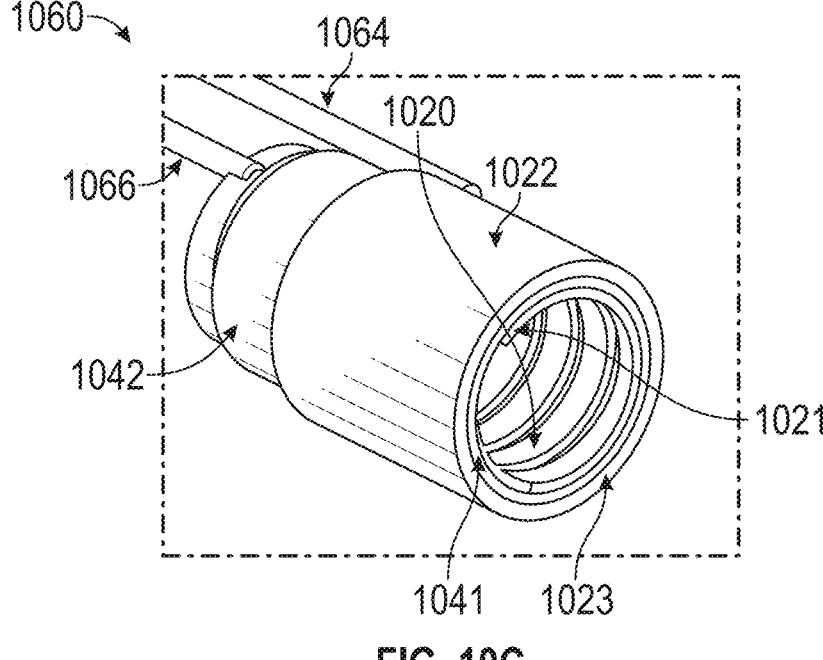
FIG. 10C shows a coaxial emitter shock wave source, according to aspects of the present disclosure.

According to an embodiment, the electrode pair of the flat wire coil can be formed from a flat coil disposed within a conductive sheath, wherein both the flat coil and the conductive sheath are each connected to an insulated wire. An exemplary flat coil emitter shock wave source, such as the shock wave source 1060 of the catheter 1000 is shown in FIG. 10C. The shock wave source 1060 includes a flat helical wire configured as a flat coil 1020, and a cylindrical conductive sheath configured as a conductive sheath 1022, separated by an insulation sheath 1042. The insulation sheath 1042 is mounted circumferentially within the conductive sheath 1022, with the flat coil 1020 disposed on an inner surface of the insulation sheath 1022 such that the flat coil 1020 and the conductive sheath 1022 form respective electrodes of an electrode pair.

The conductive sheath 1022 and the flat coil 1020 can be formed from a conductive material, such as a conductive metal. In one or more examples, the conductive sheath 1022 can be formed from an erosion resistant metal tubing, such as stainless steel, platinum, iridium, molybdenum, tungsten, or copper tubing that has been shaped into an extended tubular or cylindrical shape. The flat coil 1020 can similarly be formed from an erosion resistant metal material, such as stainless steel, platinum, iridium, molybdenum, tungsten, or copper that has been shaped into a flat helical coil. The flat coil 1020 can be any desired thickness, for example, between 0.002 and 0.003 inches thick. In one or more examples, the conductive sheath 1022 can be relatively thicker than the flat coil 1020. For instance, the conductive sheath 1022 could be approximately 0.004 to 0.006 inches thick. Alternatively, the flat coil 1020 can be thicker than the conductive sheath 1022. For example, the flat coil 1020 could be between 0.004 to 0.006 inches while the conductive sheath 1022 can be relatively thinner, e.g., between 0.002 to 0.003 inches thick.

In some embodiments, the flat coil 1020 and the conductive sheath 1022 form an electrode pair of an electrode assembly for a catheter. As shown in FIG. 10C, the flat coil 1020 has a distal end 1021 and the conductive sheath has a distal side edge 1023. The distal end 1021 of the flat coil 1020 is positioned proximate to the distal side edge 1023 of the outer conductive sheath 1022, to create an arcing region across which current can flow between the flat coil 1020 and the conductive sheath 1022. In one or more examples, current flowing across this arcing region can generate shockwaves inside the catheter.

As seen in FIG. 10C, the flat coil 1020 and the conductive sheath 1022 are separated by the insulator sheath 1042. The insulating sheath 1042 can be formed from a non-conductive insulating material that prevents unintended current flow between certain regions of the flat coil 1020 and the conductive sheath 1022. In one or more examples, the insulator sheath 1042 can block any flow of current between the flat coil 1020 and the conductive sheath 1022 along the length of the insulator sheath 1042. Because current is prevented from flowing between the flat coil 1020 and the conductive sheath 1022 along the length of the insulator sheath 1042, the current can only flow across the arcing region between the distal end 1023 of the conductive sheath 1022 and the distal end 1021 of the flat coil 1020. In one or more examples, the insulator sheath 1042 can be formed from a polymeric material, e.g., a polyimide, that is shaped into an extended tubular or cylindrical shape. In one or more examples, the insulator sheath 1042 can be approximately 0.002 to 0.004 inches thick.

As shown in FIG. 10C, the insulator sheath 1042 has a distal side edge 1041. In one or more examples, the distal side edge 1041 of the insulator sheath 1042 can be proximate to (e.g., flush with) the distal side edges of the conductive sheath 1022 and/or the flat coil 1020. The proximal side edge of the insulator sheath 1042 can extend beyond the proximal side edge of at least one of the conductive sheath 1022 and the flat coil 1020 to prevent unintended current flow between the proximal side edges of the conductive sheath 1022 and the flat coil 1020. The shape and position of the insulating sheath 1042 can ensure that the arcing region between the flat coil 1020 and the conductive sheath 1022 (e.g., the path of least resistance for current flow, normally the closest distance between the flat coil and the sheath) is between the distal end 1021 and the distal side edge 1023 of the flat coil 1020 and the conductive sheath 1022, respectively. In one or more examples, the arcing region will initially begin more particularly at the distal end 1021 of the flat coil 1020 that is located at the very end of the coil.

As seen in FIG. 10C, the shock wave source 1060 can also include two insulated wires 1066, 1064, extending along the length of the catheter. In particular, a first insulated wire 1066 can be electrically connected to the flat coil 1020, and a second insulated wire 1064 can be electrically connected to the conductive sheath 1022. In one or more examples, the insulated wires 1066, 1064, can provide an electrical connection between the flat coil 1020, the conductive sheath 1022, and an external voltage source, e.g., a high voltage pulse generator (not pictured). In one or more examples, the flat coil 1020 can be connected to a positive terminal of the voltage source, with the conductive sheath 1022 connected to a negative terminal of the voltage source or to ground. Alternatively, the flat coil 1020 can be connected to a negative terminal of the voltage source or to ground while the conductive sheath is connected to a positive terminal of the voltage source. The conductive portions of the wires 1066, 1064 can be heat-sealed or otherwise fixed to the conductive sheath 1022 and the flat coil 1020 to provide a direct electrical connection. In one or more examples, the insulated wires 1066, 1064 can extend within a fluid lumen of the catheter, e.g., fixed to a side-wall of the lumen or disposed within grooves extending along the lumen. The wires 1066, 1064 can also extend through a separate lumen of the catheter, e.g., a wire lumen. In one or more examples, the wires 1066, 1064 can be insulated copper wires.

A series of high voltage pulses can be transmitted across the wires 1066, 1064 by an external voltage source, e.g., a pulsed high voltage source, to generate a series of shockwaves at the shock wave source 1060. Negative and positive terminals of the external voltage source can be connected to the proximal ends of the first insulated wire 1066 and the second insulated wire 1064, thereby creating a potential difference across the flat coil 1020 and the conductive sheath 1022 (i.e., an electrode pair of the electrode assembly) when high voltage pulses are delivered across the wires 1066, 1064. The potential difference can cause current to flow between the electrode pair to generate shockwaves. In one or more examples, the direction of the current flow can be dependent on the polarity of the electrodes, with current flowing from the more positively charged electrode (i.e., the electrode connected to the positive terminal of the voltage source via one of the wires 1066, 1064) to the more negatively charged electrode (i.e., the electrode connected to the negative terminal of the voltage source via one of the wires 1066, 1064). The duration and magnitude of each of the voltage pulses can be sufficient to generate a gas bubble at the surface of the electrodes (i.e., on the distal end 1021 of the flat coil 1020 and the distal side edge 1023 of the conductive sheath 1022).

Figure 11A:
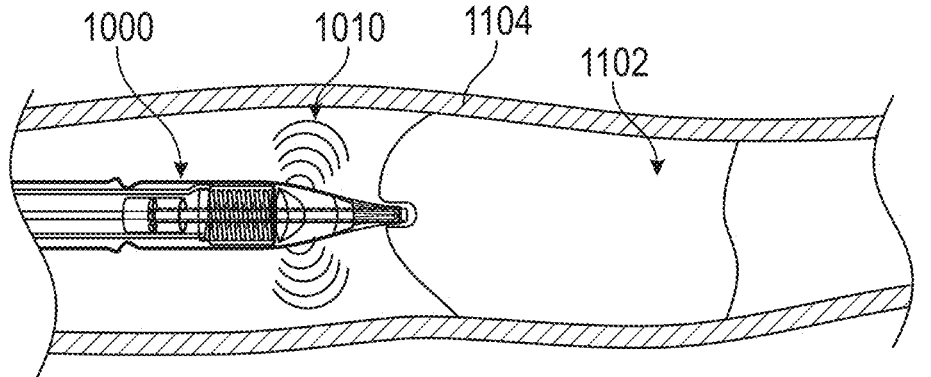
FIG. 11A is an illustration of a catheter of FIG. 10A being used to treat total occlusion in a body lumen, according to aspects of the present disclosure.
Figure 11B:
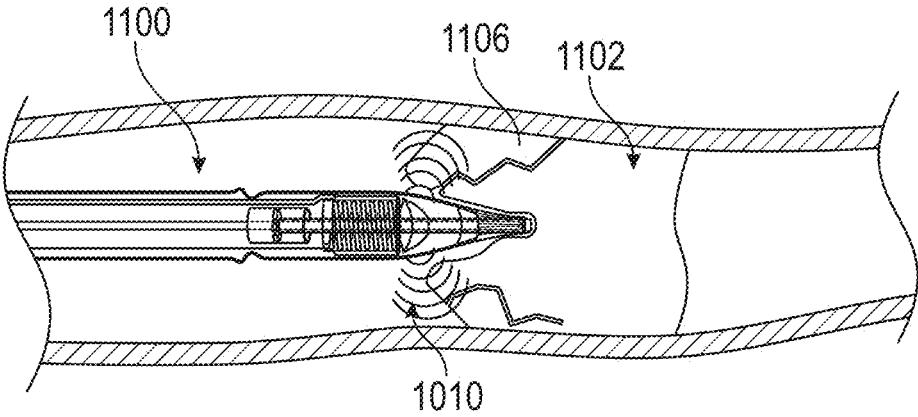
FIG. 11B is an illustration of a catheter of FIG. 10A being used to break up a total occlusion in a body lumen, according to aspects of the present disclosure.

FIGS. 11A-B illustrate the catheter 1000 of FIGS. 10A-B being used to treat a total occlusion in a body lumen. As discussed above, when the shock wave source 1060 of the catheter 1000 generates shock waves that impinge on the deflector 1040, the impactor 1030 can create a "jackhammer" effect based on axial translation of the distal tip 1035 of the impactor 1030. FIG. 11A depicts the catheter 1000 actively harnessing this jackhammer effect to effectively drill into an occluded area 1102 within a body lumen 1104. As the catheter 1000 proceeds further forward into the occlusion 1102, the transversely propagated shock waves (e.g., the shock waves that are deflected in a transverse direction after impinging on a back side of the deflector 1040) help to break up the occlusion 1102, as shown by the fissures 1106 depicted in FIG. 11B. Thus, FIG. 11A shows the catheter 1000 creating a channel into the occluded area 1102, and FIG. 11B shows the catheter 1000 enlarging that channel which both enables the catheter 1000 to proceed further into the occluded area 1102 and facilitates breaking up the occluded area 1102. Accordingly, the catheter 1000 can be configured to harness both forward-directed jack-hammering and transverse shock wave energy to treat regions of body lumen both proximal to the distal end 1024 of the catheter 1000 and adjacent to the catheter body 1020.

It should be noted that the elements and features of the example catheters discussed above may be rearranged, recombined, and modified without departing from the present invention. For instance, while a number of shockwave sources have been discussed above, a catheter according to the present invention can be configured to use a variety of electrode configurations to generate shockwaves, and the number, placement and spacing of the electrode pairs can be modified without departing from the subject invention. Further, while FIG. 7 illustrates one example method, the steps of the method may be rearranged, reordered, removed, or modified without departing from the subject invention.

It will be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A catheter for treating an occlusion in a body lumen, the catheter comprising:
   a catheter body having a distal end, the catheter body being fillable with a fluid;
   an impactor connected to the distal end of the catheter body, the impactor having a proximal end inside the catheter body and a distal end outside the catheter body;
   a shock wave source comprising an electrode pair configured to generate a shock wave; and
   a deflector coupled to the proximal end of the impactor in between the shock wave source and the distal end of the catheter body, wherein, when the shock wave source generates a shock wave, the shock wave impinges on the deflector causing the deflector to advance relative to the catheter body in a distal direction in conjunction with the impactor such that the distal end of the impactor delivers a mechanical force to the occlusion.

2. The catheter of claim 1, wherein the distal end of the catheter body comprises a flexible material that causes the impactor to move proximally relative to the catheter body after the shock wave has terminated.

3. The catheter of claim 1, wherein, when the shock wave source generates a shock wave, the deflector is configured to advance distally between 50 μm and 100 μm.

4. The catheter of claim 1, wherein, when the shock wave source generates a shock wave, the deflector deflects a portion of shock wave energy in a direction transverse to the catheter.

5. The catheter of claim 1, wherein the catheter body has a longitudinal axis, and the deflector includes a proximal surface that faces the shock wave source, and a deflector angle is defined between the proximal surface of the deflector and the longitudinal axis of the catheter body, the deflector angle being between 120° and 150°.

6. The catheter of claim 1, further comprising:

a cylinder mounted within the catheter body; and a shaft mounted to a proximal end of the deflector, wherein the shaft is configured to slide within the cylinder.

7. The catheter of claim 6, further comprising a spacer that projects outward between the shaft and the cylinder to retain the shaft at a center of the cylinder.

8. The catheter of claim 1, wherein the impactor includes a laser-cut metal tube.

9. The catheter of claim 1, wherein the impactor includes a guide wire lumen sized to receive a guide wire.

10. The catheter of claim 1, further comprising a tapered distal tip coupled to the distal end of the catheter body, wherein the tapered distal tip is configured to advance in the distal direction in conjunction with the deflector and the impactor to deliver the mechanical force to the occlusion.

11. The catheter of claim 10, wherein the tapered distal tip comprises a rigid material.

12. The catheter of claim 1, wherein the catheter body comprises a plurality of folds disposed on the catheter body, the plurality of folds configured to expand to an unfolded position in response to generation of a shock wave and to return to a folded position after the shock wave has terminated.

13. The catheter of claim 12, wherein the catheter body comprises a vibrating section in between the folds and the distal end of the catheter body and a stationary section located on a proximal end of the catheter body that terminates at the folds; and wherein the vibrating section is configured to move in the distal direction as the folds expand to the unfolded position and to move proximally relative to the catheter body when the folds return to the folded position.

14. The catheter of claim 1, wherein the shock wave source comprises a cylindrical inner conductive sheath mounted within the catheter, the cylindrical inner conductive sheath having a distal side edge;

a cylindrical outer conductive sheath mounted circumferentially around the cylindrical inner conductive sheath within the catheter, the cylindrical outer conductive sheath having a distal side edge proximal to the distal side edge of the cylindrical inner conductive sheath; and an insulation sheath mounted within the catheter between the cylindrical outer conductive sheath and the cylindrical inner conductive sheath;

wherein, when voltage pulses are applied across the cylindrical inner conductive sheath and the cylindrical outer conductive sheath, current flows across an arcing region between the cylindrical inner conductive sheath and the cylindrical outer conductive sheath to generate shock waves.

15. The catheter of claim 1, wherein the shock wave source comprises:

a cylindrical conductive sheath mounted within the catheter, the cylindrical conductive sheath having a distal side edge;

an insulation sheath mounted circumferentially within the cylindrical conductive sheath, the insulation sheath having a distal side edge proximal to the distal side edge of the cylindrical conductive sheath;

a flat coil disposed on an inner surface of the insulation sheath and the distal side edge of the insulation sheath; and wherein when voltage pulses are applied across the flat coil and the cylindrical conductive sheath, current flows across an arcing region between the flat coil and the cylindrical conductive sheath to generate shock waves.

16. A catheter for treating an occlusion in a body lumen, the catheter comprising:

a catheter body having a distal end, the catheter body being fillable with a fluid;

an impactor connected to the distal end of the catheter body, the impactor having a proximal end inside the catheter body and a distal end outside the catheter body;

a shock wave source comprising at least one optical fiber configured to generate a shock wave; and a deflector coupled to the proximal end of the impactor in between the shock wave source and the distal end of the catheter body, wherein, when the shock wave source generates a shock wave, the shock wave impinges on the deflector causing the deflector to advance relative to the catheter body in a distal direction in conjunction with the impactor such that the distal end of the impactor delivers a mechanical force to the occlusion.

17. The catheter of claim 16, wherein the distal end of the catheter body comprises a flexible material that causes the impactor to move proximally relative to the catheter body after the shock wave has terminated.

18. The catheter of claim 16, wherein, when the shock wave source generates the shock wave, the deflector is configured to advance distally between 50 μm and 100 μm.

19. The catheter of claim 16, wherein, when the shock wave source generates the shock wave, the deflector deflects a portion of shock wave energy in a direction transverse to the catheter.

20. The catheter of claim 16, wherein the catheter body has a longitudinal axis, and the deflector includes a proximal surface that faces the shock wave source, and a deflector angle is defined between the proximal surface of the deflector and the longitudinal axis of the catheter body, the deflector angle being between 120° and 150°.

21. The catheter of claim 16, further comprising:

a cylinder mounted within the catheter body; and a shaft mounted to a proximal end of the deflector, wherein the shaft is configured to slide within the cylinder.

22. The catheter of claim 21, further comprising a spacer that projects outward between the shaft and the cylinder to retain the shaft at a center of the cylinder.

23. The catheter of claim 16, wherein the shock wave source is optically coupled to a laser that generates pulses of light, said pulses of light being emitted from the at least one optical fiber.

24. The catheter of claim 16, wherein the impactor includes a laser-cut metal tube.

25. The catheter of claim 16, wherein the impactor includes a guide wire lumen sized to receive a guide wire.

26. The catheter of claim 16, further comprising a tapered distal tip coupled to the distal end of the catheter body, wherein the tapered distal tip is configured to advance in the distal direction in conjunction with the deflector and the impactor to deliver the mechanical force to the occlusion.

27. The catheter of claim 26, wherein the tapered distal tip comprises a rigid material.

28. The catheter of claim 16, wherein the catheter body comprises a plurality of folds disposed on the catheter body, the plurality of folds configured to expand to an unfolded position in response to generation of the shock wave and to return to a folded position after the shock wave has terminated.

29. The catheter of claim 28, wherein the catheter body comprises a vibrating section in between the folds and the distal end of the catheter body and a stationary section located on a proximal end of the catheter body that terminates at the folds; and wherein the vibrating section is configured to move in the distal direction as the folds expand to the unfolded position and to move proximally relative to the catheter body when the folds return to the folded position.

30. A method of treating an occlusion in a body lumen, comprising:

positioning an impactor adjacent to the occlusion in the body lumen, and energizing a shock wave source to generate a shock wave within a catheter body filled with a fluid, wherein the shock wave impinges on a deflector coupled to the impactor within the catheter body to advance the impactor in a first direction to deliver a mechanical force to the occlusion.

31. The method of claim 30, further comprising:

stretching a flexible material of the catheter body as the impactor is advanced, wherein the flexible material causes the impactor to move in a second direction opposite the first direction after the shock wave is terminated.

32. The method of claim 30, further comprising advancing a guide wire through the catheter body and the impactor to aid in insertion and removal of the catheter body.

* * * * *